(12) United States Patent
Bharkhada et al.

(10) Patent No.: US 12,737,949 B2
(45) Date of Patent: Sep. 15, 2026

(54) SYSTEMS AND METHODS OF ACCELERATED DYNAMIC IMAGING IN PET

(71) Applicant: Siemens Medical Solutions USA, Inc., Malvern, PA (US)

(72) Inventors: Deepak Bharkhada, Knoxville, TN (US); Maurizio Conti, Knoxville, TN (US); Vladimir Panin, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 512 days.

(21) Appl. No.: 17/806,743

(22) Filed: Jun. 14, 2022

(65) Prior Publication Data

US 2023/0401769 A1 Dec. 14, 2023

(51) Int. Cl.

*G06T 12/20* (2026.01)
*A61B 6/03* (2006.01)
*G06T 7/00* (2017.01)

(52) U.S. Cl.

CPC .............. *G06T 12/20* (2026.01); *A61B 6/037* (2013.01); *G06T 7/97* (2017.01); *G06T 2207/10104* (2013.01); *G06T 2207/20081* (2013.01); *G06T 2207/20084* (2013.01); *G06T 2207/30004* (2013.01); *G06T 2210/41* (2013.01)

(58) Field of Classification Search

CPC ..................... G06T 11/006; G06T 7/97; G06T 2207/10104; G06T 2207/20081; G06T 2207/20084; G06T 2207/30004; G06T 2210/41; G06T 2211/441; G06T 11/005; G06T 11/003; A61B 6/037; A61B 6/5205; A61B 6/5211; G06N 3/045; G06N 3/08; G06N 3/084

See application file for complete search history.

(56) References Cited

U.S. PATENT DOCUMENTS

| | | | |
|---|---|---|---|
| 8,000,513 | B2 | 8/2011 | Defrise et al. |
| 8,110,805 | B2 | 2/2012 | Panin |
| 9,990,741 | B2 | 6/2018 | Panin |
| 11,164,344 | B2 | 11/2021 | Whiteley et al. |

(Continued)

OTHER PUBLICATIONS

P. M. Joseph, "An Improved Algorithm for Reprojecting Rays through Pixel Images," in IEEE Transactions on Medical Imaging, vol. 1, No. 3, pp. 192-196, Nov. 1982, doi: 10.1109/TMI.1982.4307572. Accessed online on Nov. 15, 2024 from [https://ieeexplore.ieee.org/document/4307572] (Year: 1982).*

(Continued)

*Primary Examiner* — John Villecco
*Assistant Examiner* — Joshua B. Crockett

(57) ABSTRACT

Systems and methods of dynamic PET imaging are disclosed. A system includes a positron emission tomography (PET) imaging modality configured to execute a first scan to acquire a first PET dataset and a processor. The first PET dataset includes dynamic PET data. The processor is configured to back-project the first PET dataset to generate a plurality of histo-image frames, input each of the plurality of histo-image frames to a trained neural network, and receive a dynamic PET output from the trained neural network. Each of the histo-image frames corresponds to a first axial position of the PET imaging modality.

18 Claims, 12 Drawing Sheets

(56) References Cited

U.S. PATENT DOCUMENTS

| | | | | |
|---|---|---|---|---|
| 2015/0297168 | A1 | 10/2015 | Panin | |
| 2018/0293762 | A1 | 10/2018 | Fu et al. | |
| 2020/0051260 | A1 | 2/2020 | Shen et al. | |
| 2020/0167974 | A1* | 5/2020 | Liu | G06N 3/08 |
| 2020/0363542 | A1* | 11/2020 | Song | G01T 1/171 |
| 2021/0104079 | A1* | 4/2021 | Whiteley | G06N 3/084 |
| 2022/0015721 | A1* | 1/2022 | Shah | A61B 6/5217 |
| 2023/0102661 | A1* | 3/2023 | Hashimoto | A61B 6/5258 382/131 |
| 2024/0153166 | A1* | 5/2024 | He | G06T 11/008 |
| 2024/0242398 | A1* | 7/2024 | Xi | G06N 3/045 |
| 2024/0398361 | A1* | 12/2024 | Ye | A61B 6/037 |
| 2025/0069289 | A1* | 2/2025 | Lyu | G06T 5/70 |

OTHER PUBLICATIONS

Hou et al. “Flexible Conditional Image Generation of Missing Data with Learned Mental Maps”, arXiv.org, Aug. 29, 2019. Accessed on Jan. 23, 2026 via <https://arxiv.org/abs/1908.11312>. (Year: 2019).*

William Whitley et al., “FastPET: Near Real-Time Reconstruction of PET Histo-Image Data Using a Neural Network”, IEEE Transactions on Radiation and Plasma Medical Sciences, vol. 5, No. 1, Jan. 1, 2021, pp. 65-77.

* cited by examiner

SYSTEMS AND METHODS OF ACCELERATED DYNAMIC IMAGING IN PET

BACKGROUND

According to conventional Positron Emission Tomography (PET) imaging, a tracer compound including a radionuclide is introduced into a patient body by injection or ingestion. Radioactive decay of the radionuclide generates positrons, which eventually encounter electrons and are annihilated thereby. The annihilation event produces two gamma photons which travel in approximately opposite directions. Accordingly, an annihilation event is identified when two detectors disposed on opposite sides of the patient body detect the arrival of two oppositely-travelling gamma photons within a particular coincidence time window.

Because the two gamma photons travel in approximately opposite directions, the locations of the two detectors determine a Line-of-Response (LOR) along which the annihilation event occurred. Time-of-flight (TOF) PET measures the difference between the detection times of the two gamma photons arising from the annihilation event. This difference may be used to estimate a particular position along the LOR at which the annihilation event occurred.

In dynamic imaging in PET acquisitions of long scans and data sets are divided in successive time frames. Multiple PET images are reconstructed to study development of PET signals over time, dynamically. Dynamic imaging can be used to correct for motion, to assess distribution in different cardiac or respiratory cycles, to study tracer kinetics (also via method called parametric imaging), and other applications. The requirements of having many frames to reconstruct implies the need for a fast reconstruction to allow the images to be ready in a reasonable time.

SUMMARY

In various embodiments, a system includes a PET imaging modality configured to execute a first scan to acquire a first PET dataset and a processor. The first PET dataset includes dynamic PET data. The processor is configured to back-project the first PET dataset to generate a plurality of histo-image frames, input each of the plurality of histo-image frames to a trained neural network, and receive a dynamic PET output from the trained neural network. Each of the histo-image frames corresponds to a first axial position of the PET imaging modality.

In various embodiments, a method of dynamic imaging for a PET imaging device is disclosed. The method includes steps of executing a first scan to acquire a first PET dataset, back-projecting the first PET dataset to generate a plurality of histo-image frames, inputting each of the plurality of histo-image frames to a trained neural network, receiving a dynamic PET output from the trained neural network. The first PET dataset includes dynamic PET data and each of the histo-image frames corresponds to a first axial position of the PET imaging modality.

In various embodiments, a method of training a neural network for use in dynamic positron emission tomography (PET) imaging is disclosed. The method includes steps of receiving a training dataset comprising a plurality of dynamic PET datasets and a plurality of dynamic PET outputs, inputting each of the plurality of dynamic PET datasets to a neural network, and modifying the neural network based on differences between the estimated dynamic PET output for each dynamic PET dataset and the corresponding dynamic PET output. Each dynamic PET dataset in the plurality of dynamic PET datasets has a corresponding dynamic PET output in the plurality of dynamic PET outputs and the neural network is configured to generate an estimated dynamic PET output for each dynamic PET dataset in the plurality of dynamic PET datasets.

BRIEF DESCRIPTION OF THE DRAWINGS

The features and advantages of the present invention will be more fully disclosed in, or rendered obvious by the following detailed description of the preferred embodiments, which are to be considered together with the accompanying drawings wherein like numbers refer to like parts and further wherein.

DETAILED DESCRIPTION

Figure 1:
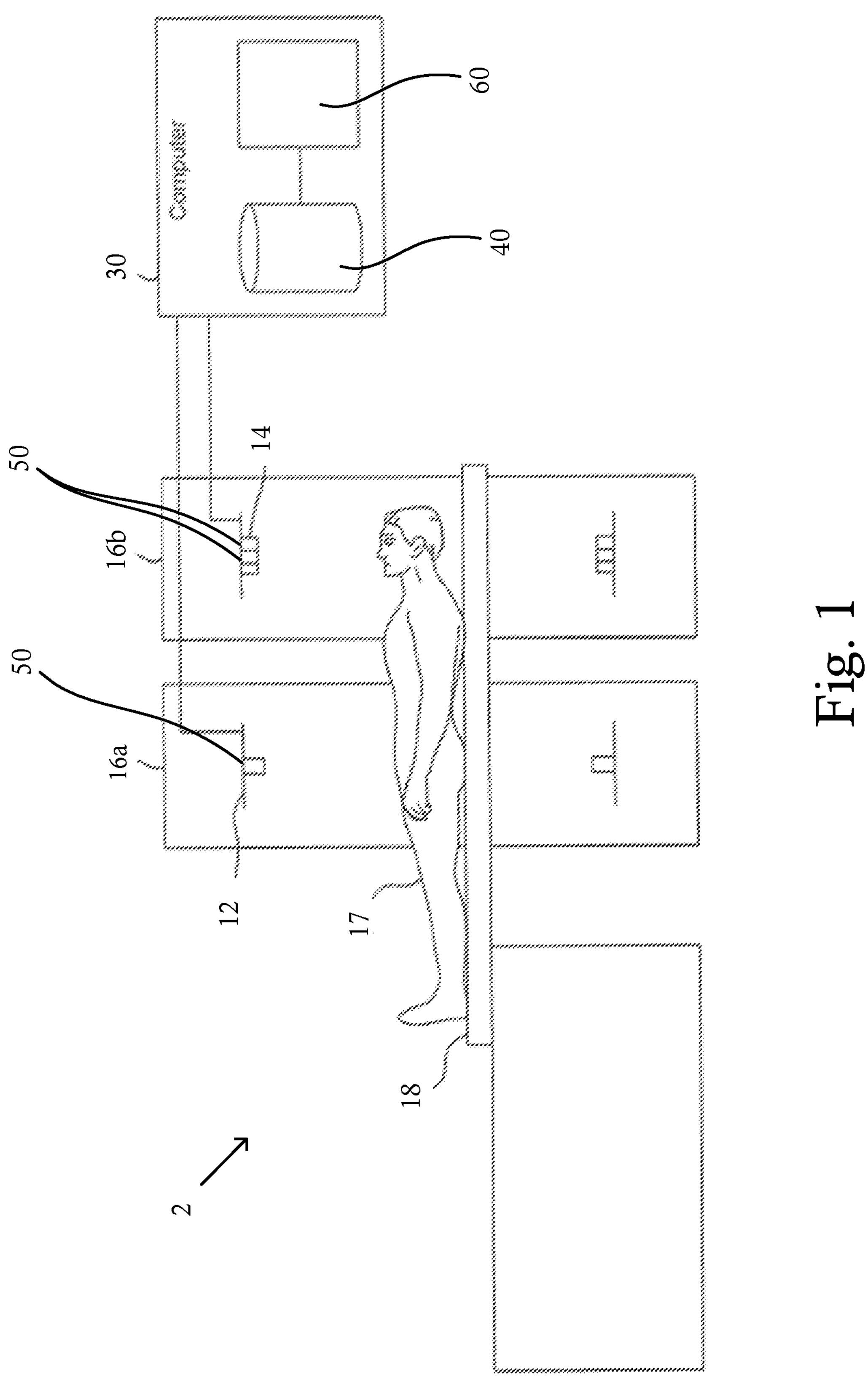
FIG. 1 illustrates a nuclear imaging system, in accordance with some embodiments.

This description of the exemplary embodiments is intended to be read in connection with the accompanying drawings, which are to be considered part of the entire written description.

In the following, various embodiments are described with respect to the claimed systems as well as with respect to the claimed methods. Features, advantages or alternative embodiments herein can be assigned to the other claimed objects and vice versa. In other words, claims for the systems can be improved with features described or claimed in the context of the methods. In this case, the functional features of the method are embodied by objective units of the systems.

Furthermore, in the following, various embodiments are described with respect to methods and systems for generating reconstructed PET images using time-referenced PET data and a trained neural network as well as with respect to methods and systems for training a neural network to generate reconstructed PET images using time-referenced PET data. Features, advantages or alternative embodiments herein can be assigned to the other claimed objects and vice versa. In other words, claims for methods and systems for training a neural network to generate reconstructed PET images using time-referenced PET data can be improved with features described or claimed in context of the methods and systems for generating reconstructed PET images using time-referenced PET data, and vice versa.

In general, a trained function mimics cognitive functions that humans associate with other human minds. In particular, by training based on training data the trained function is able to adapt to new circumstances and to detect and extrapolate patterns.

In general, parameters of a trained function can be adapted by means of training. In particular, a combination of supervised training, semi-supervised training, unsupervised training, reinforcement learning and/or active learning can be used. Furthermore, representation learning (an alternative term is "feature learning") can be used. In particular, the parameters of the trained functions can be adapted iteratively by several steps of training.

In particular, a trained function can comprise a neural network, a support vector machine, a decision tree and/or a Bayesian network, and/or the trained function can be based on k-means clustering, Qlearning, genetic algorithms and/or association rules. In particular, a neural network can be a deep neural network, a convolutional neural network or a convolutional deep neural network. Furthermore, a neural network can be an adversarial network, a deep adversarial network and/or a generative adversarial network.

In various embodiments, a neural network which deconvolves a histo-image to obtain a simulated reconstructed PET image, is disclosed. The neural network is configured to receive changing PET information, which is time-referenced over a time period, and generate a series of dynamically-generated PET images based on the time-referenced PET data. The dynamically-generated PET images are configured to provide analysis of changing body states over the time period, such as, for example, being applicable for motion correction, assessing distribution of a tracer over different cardiac and/or respiratory cycles, studying tracer kinetics, and/or other suitable applications. The dynamically-generated PET images are generated in real-time, to allow simultaneous monitoring of dynamic changes in the time-referenced PET data. Prior methods utilizing histo-images to obtain simulated reconstructed PET images require histo-images incorporating all PET data obtained at axial positions into a single histo-image and are not able to account for dynamically changing PET data. For example, U.S. Pat. No. 11,164,344, entitled "PET image reconstruction using TOF data and neural network," issued on Nov. 2, 2021 and William Whitley, et al., "FastPET: Near Real-Time Reconstruction of PET Histo-Image Data Using a Neural Network", IEEE Transactions on Radiation and Plasma Medical Sciences, vol. 5, no. 1, January 2021, are each incorporated herein by reference in their respective entireties.

FIG. 1 illustrates one embodiment of a nuclear imaging system 2, in accordance with some embodiments. The nuclear imaging system 2 includes a scanner for at least a first modality 12 provided in a first gantry 16*a*. The first modality 12 can include any suitable imaging modality, such as a positron emission tomography (PET) modality. A patient 17 lies on a movable patient bed 18 that can be movable within the first gantry 16*a*. In some embodiments, the nuclear imaging system 2 includes a scanner for a second imaging modality 14 provided in a second gantry 16*b*. The second imaging modality 14 can be any suitable imaging modality, such as, for example, PET modality, a SPECT modality, a CT modality, magnetic resonance (MR) modality, and/or any other suitable imaging modality. Each of the first modality 12 and/or the second modality 14 can include one or more detectors 50 configured to detect an annihilation photon, gamma ray, and/or other nuclear imaging event. In some embodiments, one or more of the detectors 50 generate background radiation data during a scan.

Scan data from the first modality 12 and/or the second modality 14 is stored at one or more computer databases 40 and processed by one or more computer processors 60 of a computer system 30. The graphical depiction of computer system 30 in FIG. 1 is provided by way of illustration only, and computer system 30 can include one or more separate computing devices. The nuclear imaging data sets can be provided by the first modality 12, the second modality 14, and/or can be provided as a separate data set, such as, for example, from a memory coupled to the computer system 30. The computer system 30 can include one or more processing electronics for processing a signal received from one of the plurality of detectors 50. In some embodiments, the scan data includes background radiation-based attenuation. The computer system 30 can use one or more background radiation based attenuation maps during image reconstruction to correct for background radiation attenuation.

In some embodiments, the computer system 30 is configured to generate dynamic reconstructed PET images using time-referenced dynamic PET data. The dynamic reconstructed PET images are generated based on time-references histo-image frames corresponding to fixed axial positions within a scan volume. The dynamic reconstructed PET images can be generated by a trained neural network (or function). In some embodiments, a convolution neural network is applied to generate the dynamic reconstructed PET images, although it will be appreciated that other networks can be applied.

Figure 2:
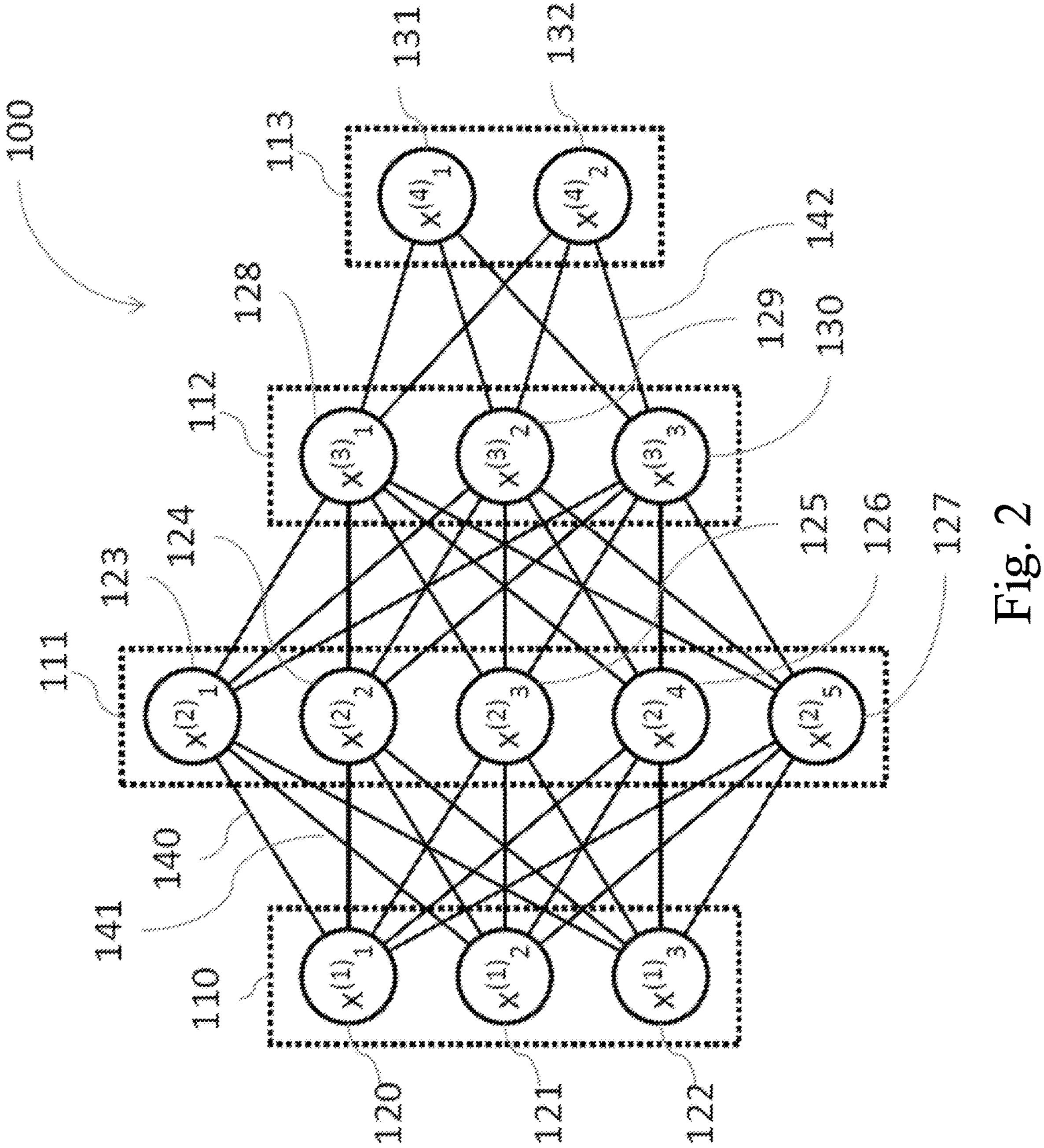
FIG. 2 illustrates an embodiment of an artificial neural network, in accordance with some embodiments.

FIG. 2 displays an embodiment of an artificial neural network 100. Alternative terms for "artificial neural network" are "neural network," "artificial neural net," "neural net," or "trained function." The artificial neural network 100 comprises nodes 120-132 and edges 140-142, wherein each edge 140-142 is a directed connection from a first node 120-132 to a second node 120-132. In general, the first node 120-132 and the second node 120-132 are different nodes 120-132, although it is also possible that the first node 120-132 and the second node 120-132 are identical. For example, in FIG. 2 the edge 140 is a directed connection from the node 120 to the node 123, and the edge 142 is a directed connection from the node 130 to the node 132. An edge 140-142 from a first node 120-132 to a second node 120-132 is also denoted as "ingoing edge" for the second node 120-132 and as "outgoing edge" for the first node 120-132.

In this embodiment, the nodes 120-132 of the artificial neural network 100 can be arranged in layers 110-113, wherein the layers can comprise an intrinsic order introduced by the edges 140-142 between the nodes 120-132. In particular, edges 140-142 can exist only between neighboring layers of nodes. In the displayed embodiment, there is an input layer 110 comprising only nodes 120-122 without an incoming edge, an output layer 113 comprising only nodes 131, 132 without outgoing edges, and hidden layers 111, 112 in-between the input layer 110 and the output layer 113. In general, the number of hidden layers 111, 112 can be chosen arbitrarily. The number of nodes 120-122 within the input layer 110 usually relates to the number of input values of the neural network, and the number of nodes 131, 132 within the output layer 113 usually relates to the number of output values of the neural network.

In particular, a (real) number can be assigned as a value to every node 120-132 of the neural network 100. Here, $x^{(n)}_i$ denotes the value of the i-th node 120-132 of the n-th layer 110-113. The values of the nodes 120-122 of the input layer 110 are equivalent to the input values of the neural network 100, the values of the nodes 131, 132 of the output layer 113 are equivalent to the output value of the neural network 100. Furthermore, each edge 140-142 can comprise a weight being a real number, in particular, the weight is a real number within the interval [−1, 1] or within the interval [0, 1]. Here, $w^{(m,n)}_{i,j}$ denotes the weight of the edge between the i-th node 120-132 of the m-th layer 110-113 and the j-th node 120-132 of the n-th layer 110-113. Furthermore, the abbreviation $w^{(n)}_{i,j}$ is defined for the weight $w^{(n,n+1)}_{i,j}$.

In particular, to calculate the output values of the neural network 100, the input values are propagated through the neural network. In particular, the values of the nodes 120-132 of the (n+1)-th layer 110-113 can be calculated based on the values of the nodes 120-132 of the n-th layer 110-113 by $$x_j^{(n+1)} = f\left(\sum_i x_i^{(n)} \cdot w_{i,j}^{(n)}\right)$$

Herein, the function f is a transfer function (another term is "activation function"). Known transfer functions are step functions, sigmoid function (e.g. the logistic function, the generalized logistic function, the hyperbolic tangent, the Arctangent function, the error function, the smooth step function) or rectifier functions. The transfer function is mainly used for normalization purposes.

In particular, the values are propagated layer-wise through the neural network, wherein values of the input layer 110 are given by the input of the neural network 100, wherein values of the first hidden layer 111 can be calculated based on the values of the input layer 110 of the neural network, wherein values of the second hidden layer 112 can be calculated based in the values of the first hidden layer 111, etc.

In order to set the values $w^{(m,n)}_{i,j}$ for the edges, the neural network 100 has to be trained using training data. In particular, training data comprises training input data and training output data (denoted as $t_i$). For a training step, the neural network 100 is applied to the training input data to generate calculated output data. In particular, the training data and the calculated output data comprise a number of values, said number being equal with the number of nodes of the output layer.

In particular, a comparison between the calculated output data and the training data is used to recursively adapt the weights within the neural network 100 (backpropagation algorithm). In particular, the weights are changed according to $$w'^{(n)}_{i,j} = w^{(n)}_{i,j} - \gamma \cdot \delta^{(n)}_j \cdot x^{(n)}_i$$

wherein γ is a learning rate, and the numbers $\delta^{(n)}_j$ can be recursively calculated as $$\delta_j^{(n)} = \left(\sum_k \delta_k^{(n+1)} \cdot w_{j,k}^{(n+1)}\right) \cdot f'\left(\sum_i x_i^{(n)} \cdot w_{i,j}^{(n)}\right)$$

based on $\delta^{(n+1)}_j$, if the (n+1)-th layer is not the output layer, and $$\delta_j^{(n)} = \left(x_k^{(n+1)} - t_j^{(n+1)}\right) \cdot f'\left(\sum_i x_i^{(n)} \cdot w_{i,j}^{(n)}\right)$$

if the (n+1)-th layer is the output layer 113, wherein f is the first derivative of the activation function, and $y^{(n+1)}_j$ is the comparison training value for the j-th node of the output layer 113.

In some embodiments, the neural network 100 is configured, or trained, to generate dynamic reconstructed PET images and/or dynamic PET parameters. For example, in some embodiments, the neural network 100 is configured to receive a plurality of histo-image frames generated from dynamic PET data at a fixed axial position within a scan volume. The neural network 100 is trained to generate dynamic reconstructed PET images or dynamic PET parameters.

Figure 3:
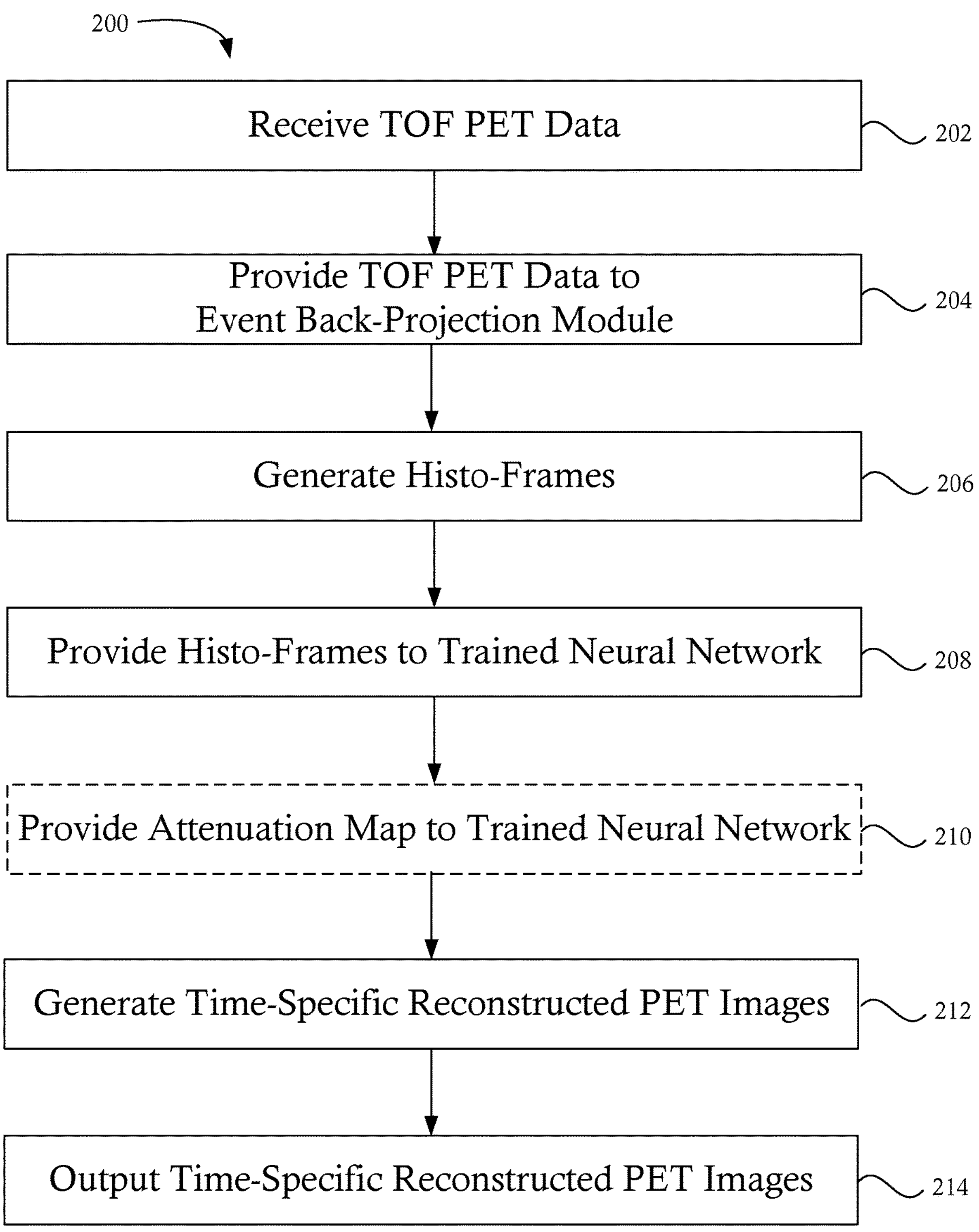
FIG. 3 is a flowchart illustrating a method of generating dynamic reconstructed PET images using time-referenced PET data and a trained neural network, in accordance with some embodiments.
Figure 4:
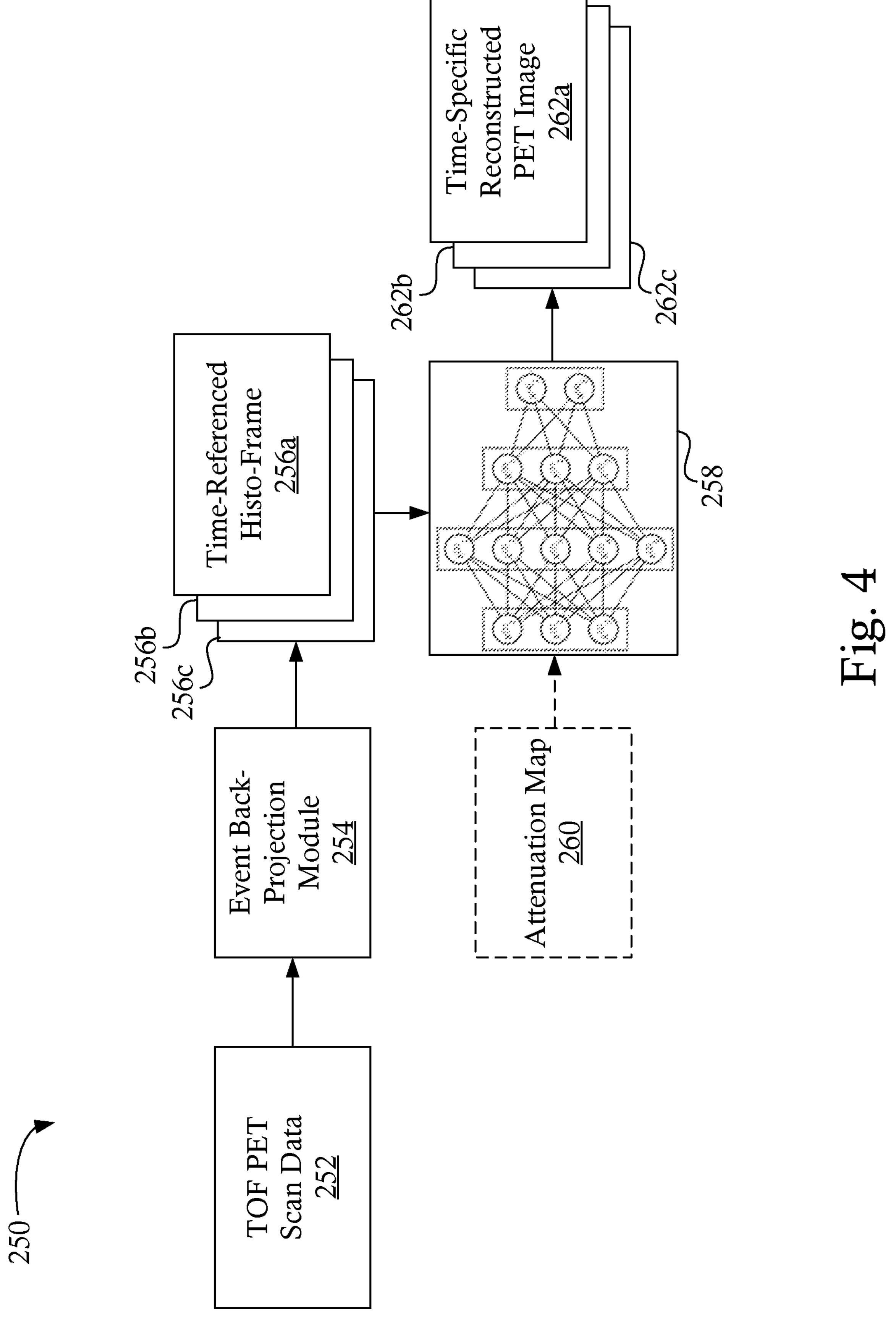
FIG. 4 is a block diagram of a system to generate a reconstructed PET image based on PET data and optional mu-maps, in accordance with some embodiments.

FIG. 3 is a flowchart 200 illustrating a method of generating dynamic reconstructed PET images using time-referenced PET data and a trained neural network configured to convert individual frames into reconstructed images, in accordance with some embodiments. FIG. 4 is a block diagram illustrating a system 250 configured to implement various portions of the method illustrated in FIG. 3, in accordance with some embodiment. The method of generating dynamic reconstructed PET images is discussed with reference to FIGS. 3 and 4.

At step 202, nuclear imaging data, and specifically TOF PET data 252, is obtained from a scanning modality, such as a PET scanning modality 12. TOF PET data 252 is obtained over a predetermined time period. The TOF PET data 252 is acquired as is known in the art. For example, TOF sinograms and/or TOF list-mode data may be acquired and/or generated by a PET scanner (e.g., imaging modality 12 and computer 30) after injection of a radioactive tracer into a subject volume (e.g., a patient or phantom). The TOF PET data 252, such as specific TOF sinograms and/or specific portions of the TOF list-mode data, correspond to a respective axial location of the subject volume over which coincident annihilation events within the volume were detected. The TOF PET data 252 includes the location of a line of response (LOR) of each coincidence event.

In some embodiments, The TOF PET data 252 includes time-references correlating specific portions of the TOF PET data 252 to specific scan times, e.g., dividing the TOF PET data 252 into frames. For example, in some embodiments, each TOF sinogram may include a time-reference, e.g., a timestamp, that identifies a specific time and/or time range at which the data within the TOF sinogram was acquired, corresponding to a single frame within the TOF PET data 252. Similarly, in embodiments including list-mode data, each entry may include a timestamp or other time-reference configured to identify the specific time at which the list-mode entry was obtained. List-mode data obtained within a given time range may correspond to a single frame within the TOF PET data 252. The time reference may be a relative time reference, such as referencing time since the start of data acquisition (e.g., the start of a scan, time since a prior data acquisition, etc.) or may be an absolute time reference (e.g., referencing an external frame of reference, such as local time, Greenwich Mean Time, etc.).

In some embodiments, position-time coordinate pairs are recorded to accurately track a position of a subject volume and time information throughout a PET imaging scan. For example, in some embodiments, the position-time coordinate pair may include position information corresponding to a position of a moveable bed, position of a moveable gantry, a position of a moveable subject volume, any other suitable position information, and/or a combination thereof. In some embodiments, for each position-time coordinate pair, the position and time are determined with respect to an initial condition (p0, t0), such as an axial initial position p0 of z=0.0 at the time t0=0 when a tracer is injected into the subject volume. The position can be accurately determined by a position sensor (e.g., a laser interferometer or the like). In some embodiments, the position-time pairs are collected at even time intervals (e.g., 10 msec or 100 msec). In other embodiments, the time intervals between position-time pairs vary with velocity (e.g., the interval can be 100 msec while the velocity is less than a threshold value, and 10 msec while the velocity is greater than the threshold value). In still other embodiments, the position-time pairs are collected at predetermined positions, such as evenly spaced and/or unevenly spaced positions.

In some embodiments, an imaging modality 12 may be operated with relative motion between the patient bed 18 and the gantry 16*a*, 16*b* in a continuous bed motion (CBM) protocol (e.g., single-direction, multiple-pass mode, a bidirectional mode, or a mixed mode) and/or a step-and-shoot protocol. The velocity can vary as a continuous function of time (e.g., saw tooth or sinusoidal), or as a discontinuous function of time (e.g., an alternating step function). The velocity can have a more complex profile; for example, the acceleration (time derivative of velocity) can be a continuous function, or can have one or more discontinuities at which the acceleration jumps or stops.

In some embodiments, the TOF PET data 252 is acquired using continuous bed motion (CBM) scanning protocols during which the velocity and/or acceleration of a bed can be constant and/or variable such that the position of the bed as a function of time is not easily calculated. Position-time coordinate pairs may be recorded periodically (e.g., a current position of the bed or other movable component is recorded at fixed time intervals) or may be recorded positionally (e.g., a current time at which the bed or other moveable component reaches predetermined positions is recorded), providing an accurate record of position versus time. The position-time coordinate pairs may be recorded within the TOF PET data 252 and/or as separate data that is later matched to the TOF PET data 252.

In some embodiments, the TOF PET data 252 corresponding to at least one fixed axial position of the scanning modality 12 changes over the predetermined time period, e.g., the TOF PET data 252 is dynamic data that represents changes at a fixed axial position within a subject volume. In typical PET scanning, the scanning modality is configured to obtain PET data over a time period that prevents or minimizes changes at axial positions and attempts to minimize changes, such as tracer concentrations, over the entire scan period. In contrast, the dynamic TOF PET data 252 is intended to capture changes over the predetermined time period at the at least one fixed axial position. The change in the TOF PET data 252 over the predetermined time period may correspond to changes caused by movement of a patient, distribution of a tracer over different cardiac and/or respiratory cycles, tracer kinetics, and/or other physiological responses.

In some embodiments, fixed axial positions are determined based on a comparison between time-references in TOF PET data 252 and a time coordinate in a position-time coordinate pair. For example, in some instances, the time corresponding to a boundary of a fixed axial position (e.g., a predetermined slice) and a midpoint of the fixed axial position may correspond to similar boundaries within slices in the TOF PET data 252, and may be aligned based on matching of the time data within the time-referenced TOF PET data 252 to the position-time coordinate pairs.

However, in some embodiments, slice boundaries within the TOF PET data 252 may be different from the boundaries described by the position-time coordinate pairs. In such embodiments, for each slice in the TOF PET data, the imaging start time is computed as the point when the slice enters the scanner field of view (FOV) based on corresponding position-time coordinate pairs. Similarly, for each image slice, the imaging end time is computed as the point when the slice leaves the scanner FOV, based on position-time coordinate pairs. The imaging duration of the slice is defined as the difference between the imaging start time and imaging end time for the slice. The image slice reference time is then calculated as the time point when the average activity occurs due to tracer decay, while assuming no activity change due to tracer kinetics over that time duration.

A time-referenced sinogram includes a data array of an angle versus a displacement of each LOR within a specific time period at a specific axial position of the subject volume. Each time-referenced TOF sinogram includes one row containing the LOR for a particular azimuthal angle q. Each of these rows corresponds to a one-dimensional parallel projection of the tracer compound distribution at a different coordinate. List-mode data includes the coordinates of each detected coincidence event.

At step 204, the TOF PET data 252 is provided in real-time, or near-real time, to an event back-projection module 254. At step 206, the event back-projection module 254 applies a back-projection algorithm to the TOF PET data 252 to generate time-referenced histo-image frames 256*a*-256*c*. Each of the generated time-referenced histo-image frames 256*a*-256*c* includes a blurred image of the expected distribution (e.g., a histo-image) at a specific axial location of the subject volume.

The event back-projection module 254 may be configured to apply any suitable back-projection algorithm, for example, as determined by the format of the received TOF PET data 252, e.g., sinogram or list-mode data. The generated time-referenced histo-image frames 256*a*-256*c* correspond to the same axial position with respect to a subject volume (e.g., patient or phantom) that is the target of the PET data acquisition. The time-referenced histo-image frames 256*a*-256*c* may be divided over a predetermined time period at set intervals and/or may be divided at variable intervals. The intervals may be determined prior to performing TOF PET data acquisition and/or may be adjusted during TOF PET data acquisition to obtain TOF PET data 252 at specific axial positions and specific times (e.g., during specific phases of a respiratory and/or cardiac cycle).

For example, when the TOF PET data 252 includes time-referenced sinograms, the event back-projection module 254 may apply Joseph's method (P. M. Joseph, "An improved algorithm for reprojecting rays through pixel images," *IEEE Transactions on Medical Imaging*, vol. 1 no. 3, pp. 192-196, November 1982, which is incorporated herein by reference in its entirety) to generate the histo-image frames 256a-256c. As another example, when the TOF PET data 252 includes time-referenced list-mode data, the event back-projection module 254 may assign events within a predetermined time frame and/or range to an image voxel along a LOR, according to its timing information within the predetermined range. Histo-image frames generated by back-projecting list-mode data may be more accurate than histo-image frames generated by back-projecting sinograms generated from list-mode data as the list-mode data may exhibit higher-resolution timing data than TOF sinogram data generated therefrom.

In some embodiments, the TOF PET data 252, whether in sinogram or list-mode form, may be corrected using attenuation correction and/or normalization factors before back-projecting to obtain a modified histo-image frame 256a-256c. In such cases, the modified histo-image frames 256a-256c are provided as input to the trained neural network 258, as discussed below.

At step 208, each of the time-referenced histo-image frames 256a-256c is provided to a trained neural network 258. The time-referenced histo-image frames 256a-256c may be provided sequentially, e.g., as they are generated by the event back-projection module 254. As discussed in greater detail below, the trained neural network 258 is generated through an iterative training process using a training data set including time-referenced histo-image frames and/or time-referenced TOF PET data and correlated reconstructed images (e.g., ground-truth images, clinical images generated using prior art methods, etc.). The trained neural network 258 is configured to receive time-referenced histo-image frames 256a-256c corresponding to at least one fixed axial position of the subject volume.

At optional step 210, the trained neural network 258 receives an attenuation map 260, such as a mu-map. Each attenuation map 260 corresponds to the axial position and/or time-reference of one of the time-referenced histo-image frames 256a-256c. The attenuation map 260 may be derived from a second imaging process implemented by a separate imaging modality, such as a CT scan performed during the same imaging session as the PET scan from which the time-referenced TOF PET data 252 were derived, as is known in the art. Inclusion of an attenuation map 260 in the image reconstruction process implemented by the trained neural network 258 may provide higher quality images than otherwise, due to the additional structural information provided by the attenuation map 260.

At step 212, the trained neural network 258 generates time-specific reconstructed PET images 262a-262c. The time-specific reconstructed PET images 262a-262c include reconstructed images at a specific axial position of the subject volume at a predetermined time corresponding to the time of the input histo-image frame 256a-256c. Each of the time-specific reconstructed PET images 262a-262c represents the subject volume at the axial position at a specific instance in time during the PET scan. The trained neural network 258 applies a trained function to a received time-referenced histo-image frame 256a-256c to generate the corresponding time-specific reconstructed PET image 262a-262c. In embodiments including an attenuation map 260, the trained neural network 258 is configured to apply attenuation correction during reconstruction.

By virtue of the trained function, and according to some embodiments, each of the generated time-specific reconstructed PET images 262a-262c will be similar in quality and resolution to ground-truth images used to generate the trained neural network 258. In some embodiments, the trained neural network 258 is configured to generate time-specific reconstructed PET images 262a-262c in near-real time, allowing the time-specific reconstructed PET images 262a-262c to be reviewed as the corresponding scan progresses, providing real-time clinical information. In some embodiments, the trained neural network 258 is configured to apply an anatomy guided reconstruction process. For example, in some embodiments, the trained neural network 258 is trained to mimic portions of a Bowsher reconstruction. At step 214, the time-specific reconstructed PET images 262a-262c are output for use in further clinical operations, such as, for example, reviewing dynamic aspects of the subject volume over the scan period.

Figure 5:
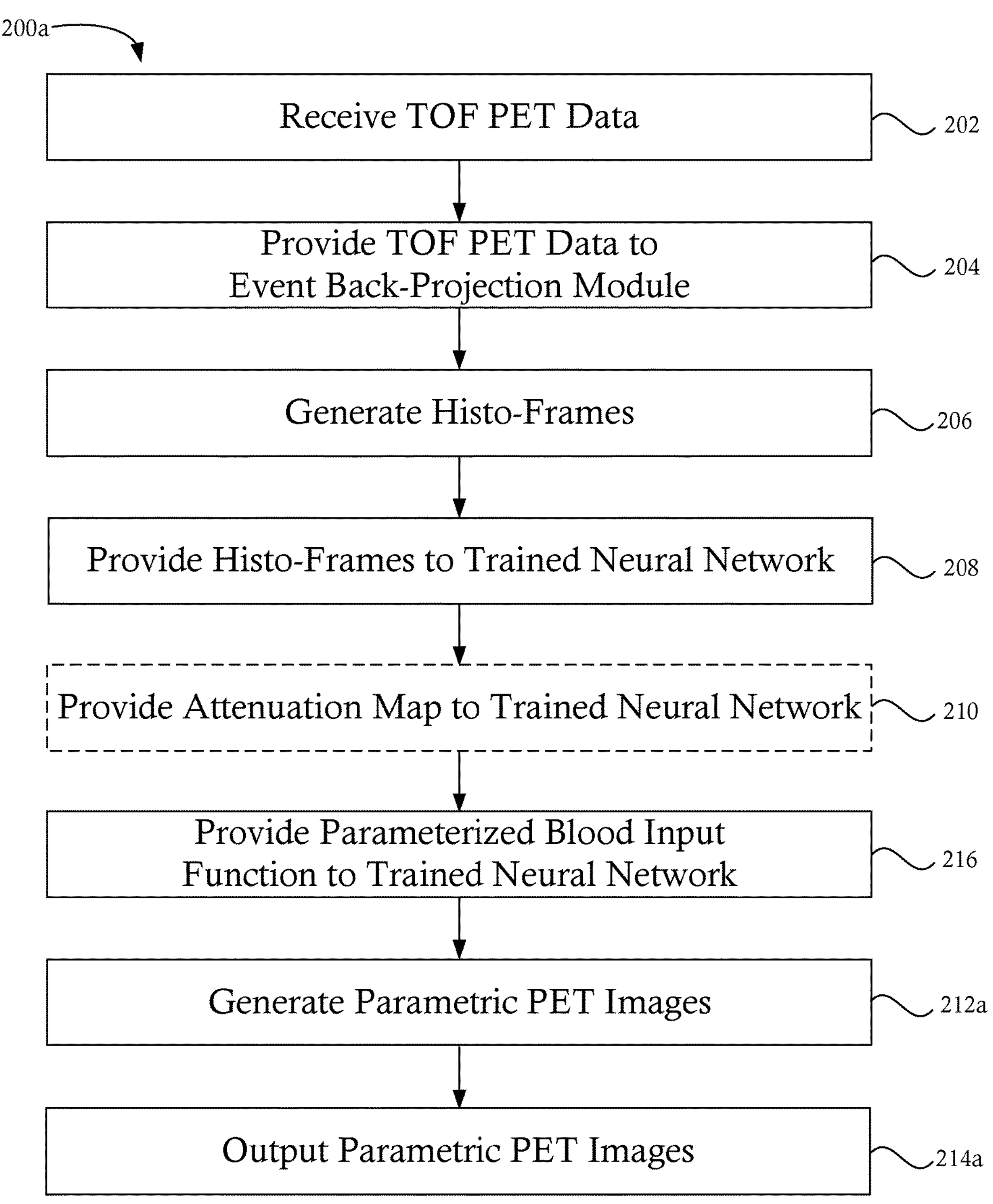
FIG. 5 is a flowchart illustrating a method of estimating parametric images from histo-image frames using a trained neural network, in accordance with some embodiments.
Figure 6:
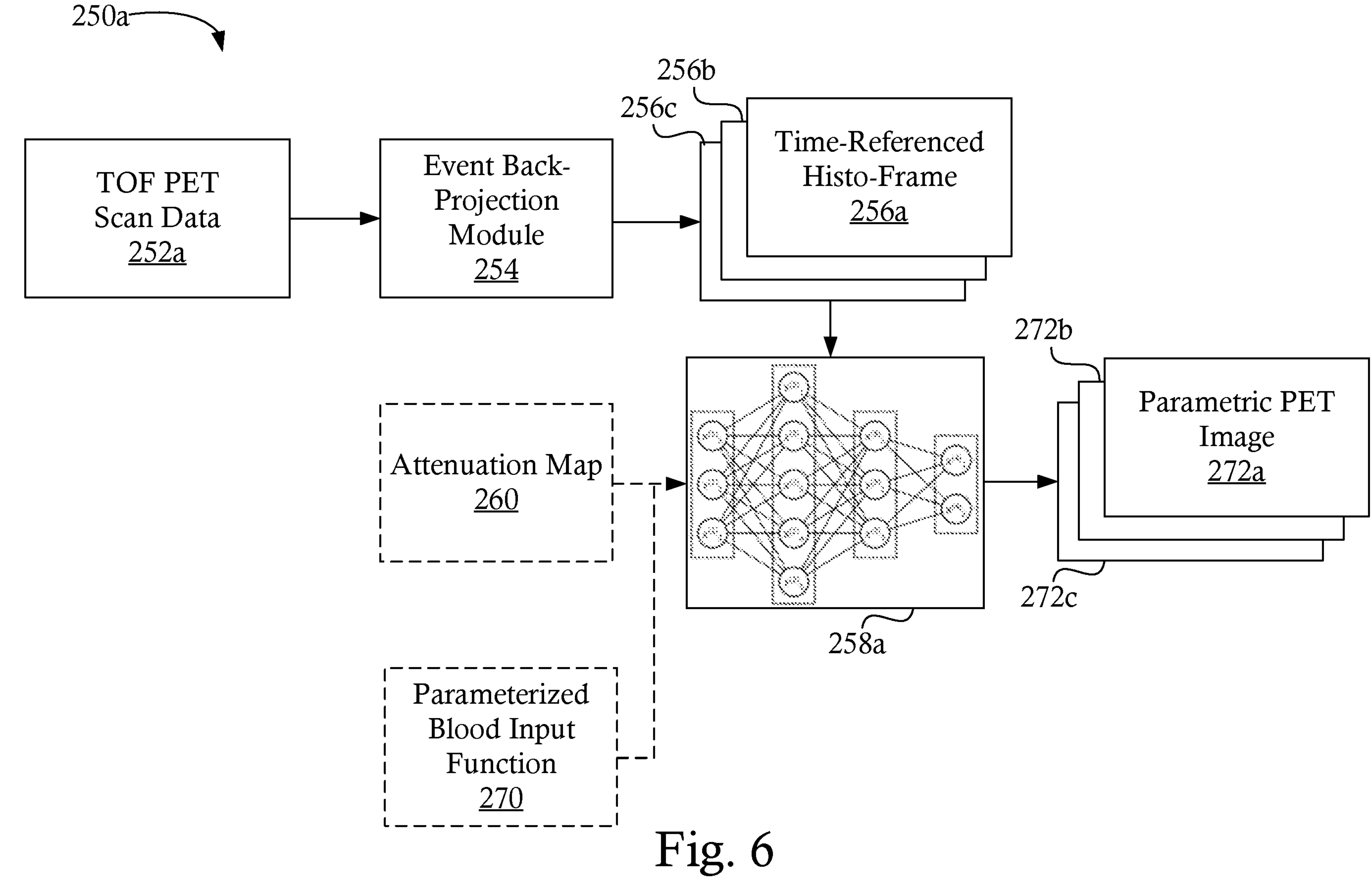
FIG. 6 is a block diagram illustrating a system configured to implement various portions of the method illustrated in FIG. 5, in accordance with some embodiments.

FIG. 5 is a flowchart 200a illustrating a method of estimating parametric images from histo-image frames using a trained neural network, in accordance with some embodiments. FIG. 6 is a block diagram illustrating a system 250a configured to implement various portions of the method illustrated in FIG. 5, in accordance with some embodiments. The method of estimating parametric images is discussed with reference to FIGS. 5 and 6. The method of estimating parametric images is similar to the method of generating dynamic reconstructed PET images using time-referenced PET data and a trained neural network configured to convert individual frames into reconstructed images discussed above with respect to FIG. 3. Similarly, the system 250a is similar to the system 250 discussed above with respect to FIG. 4. Similar description for the method and system is not repeated herein.

The method of estimating parametric images proceeds through steps 202-210 discussed above with respect to FIG. 3. Accurate imaging time information is important for accurate results for estimated parametric imaging, since kinetic parameters, for example, metabolism rate, respiratory and/or cardiovascular phase, etc., are closely correlated to time information. The tracked time information in the time-referenced PET image data 252a provides a mechanism for tracking dynamic changes during data acquisition and to synchronize additional parameters, such as a blood input function, with the dynamic PET data.

In some embodiments, the time-referenced TOF PET image data 252a is generated using one or more scan modes including, but not limited to, continuous bed motion (CBM) scans (such as single-direction, multi-scan motion, bidirectional motion, or combinations therefore), step-and-shoot scans, and/or static scans. Each of the CBM and/or step-and-shoot modes can include variable and/or fixed velocity profiles. Ideally, parametric images obtained by different scan modes should be identical since underlying physiology is independent of the scan. However, if scans are not accurately tracked and time information is not properly taken into account, the parametric images may vary. Various CBM scanning protocols are discussed in U.S. Pat. No. 10,722,189, entitled "System and method for Whole Body Continuous Bed motion Parametric PET With Flexible Scan Modes," issued on Jul. 28, 2020, the disclosure of which is incorporated herein by reference in its entirety.

In some embodiments, a trained neural network 258a is configured to utilize time-accurate information, such as position-time pairs as discussed above, to generate parametric images based on histo-image frames 256a-256c. As discussed in greater detail below, the trained neural network 258a is generated through an iterative training process using a training data set including time-referenced histo-image frames and/or time-referenced TOF PET data and correlated parametric images (e.g., parametric images generated using prior art methods). The trained neural network 258a is configured to receive time-referenced histo-image frames 256*a*-256*c* corresponding to at least one fixed axial position of the subject volume.

In some embodiments, a trained neural network 258*a* is configured to generate two parametric images: one for metabolism rate (abbreviated as "Ki") and one for distribution volume (abbreviated as "dv"). In some embodiments, to calculate kinetics rate, a CBM system records accurate time and position information, in the form of position-time coordinate pairs, as discussed above. Axial position information identifying fixed axial positions corresponding to histo-image frames 256*a*-256*c* that are provided to the trained neural network may vary from voxel to voxel.

At optional step 216, the trained neural network 258*a* is configured to receive at least one parameterized blood input function 270. The parameterized blood input function 270 may be used to assist in reconstruction of parametric images from the received histo-image frames 256*a*-256*c*.

At step 212*a*, the trained neural network 258*a* generates estimated parametric images 272*a*-272*c*. The estimated parametric PET images 272*a*-272*c* include parametric images at a specific axial position of the subject volume corresponding to the input histo-image frames 256*a*-256*c*. Each of the estimated parametric PET images 272*a*-272*c* represents a parametric image of the subject volume at the axial position during the PET scan. The trained neural network 258*a* applies a trained function to a received time-referenced histo-image frame 256*a*-256*c* to generate the corresponding estimated parametric PET images 272*a*-272*c*. In some embodiments, the trained neural network 258*a* is configured to apply attenuation correction during reconstruction using an attenuation map 260 and/or is configured to utilize a parameterized blood input function 270 during reconstruction. At step 214*a*, the parametric PET images 272*a*-272*c* are output for use in further clinical operations, such as, for example, reviewing dynamic aspects of the subject volume over the scan period.

By virtue of the trained function, and according to some embodiments, each of the generated estimated parametric images 272*a*-272*c* will be similar in quality and resolution to parametric images used to generate the trained neural network 258*a*. In some embodiments, the trained neural network 258*a* is configured to generate estimated parametric images 272*a*-272*c* in near-real time, allowing the estimated parametric images 272*a*-272*c* to be reviewed as the corresponding scan progresses, providing real-time clinical information.

Figure 7:
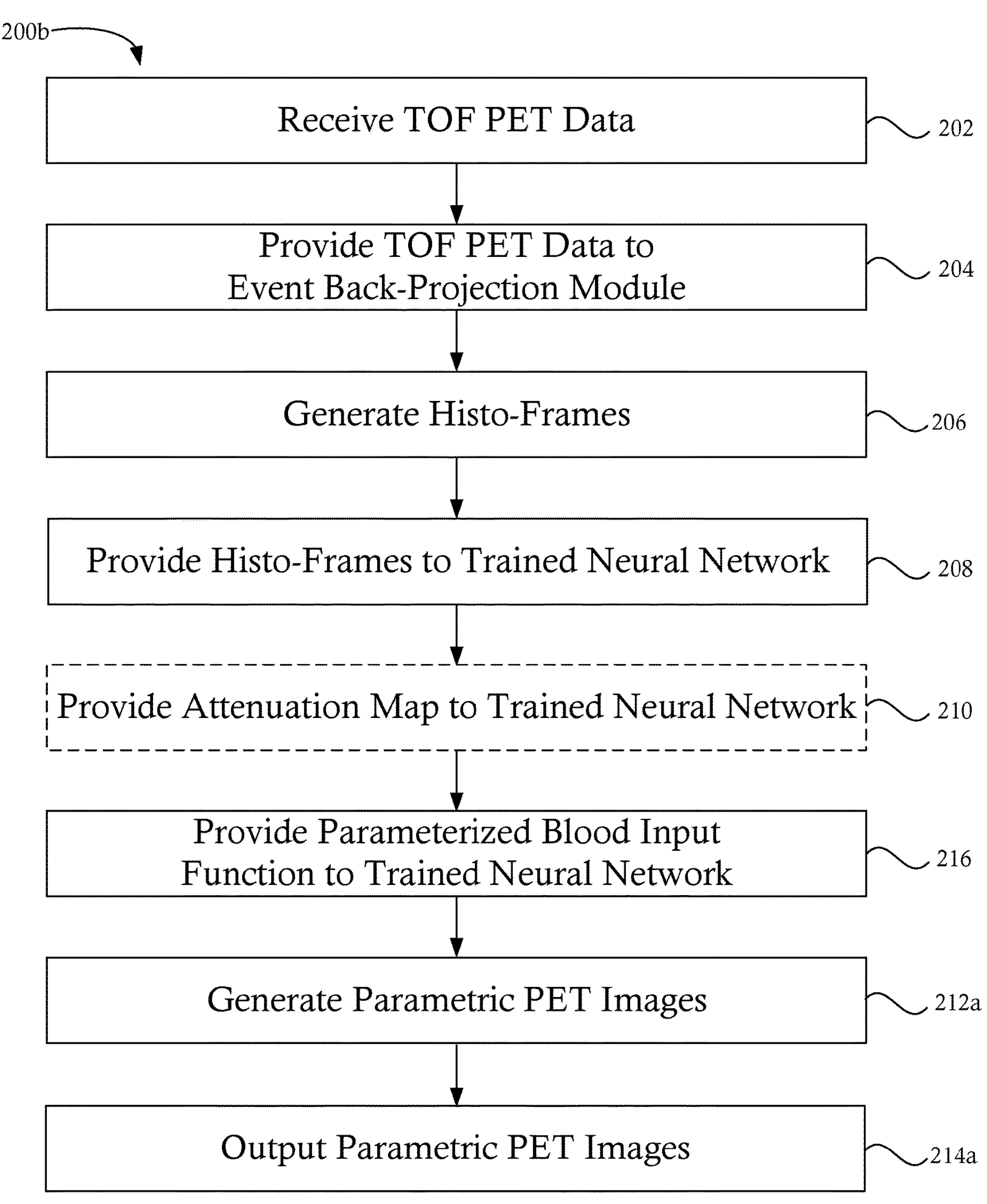
FIG. 7 is flowchart illustrating a method of generating dynamic parameters of a PET scan using a trained neural network, in accordance with some embodiments.
Figure 8:
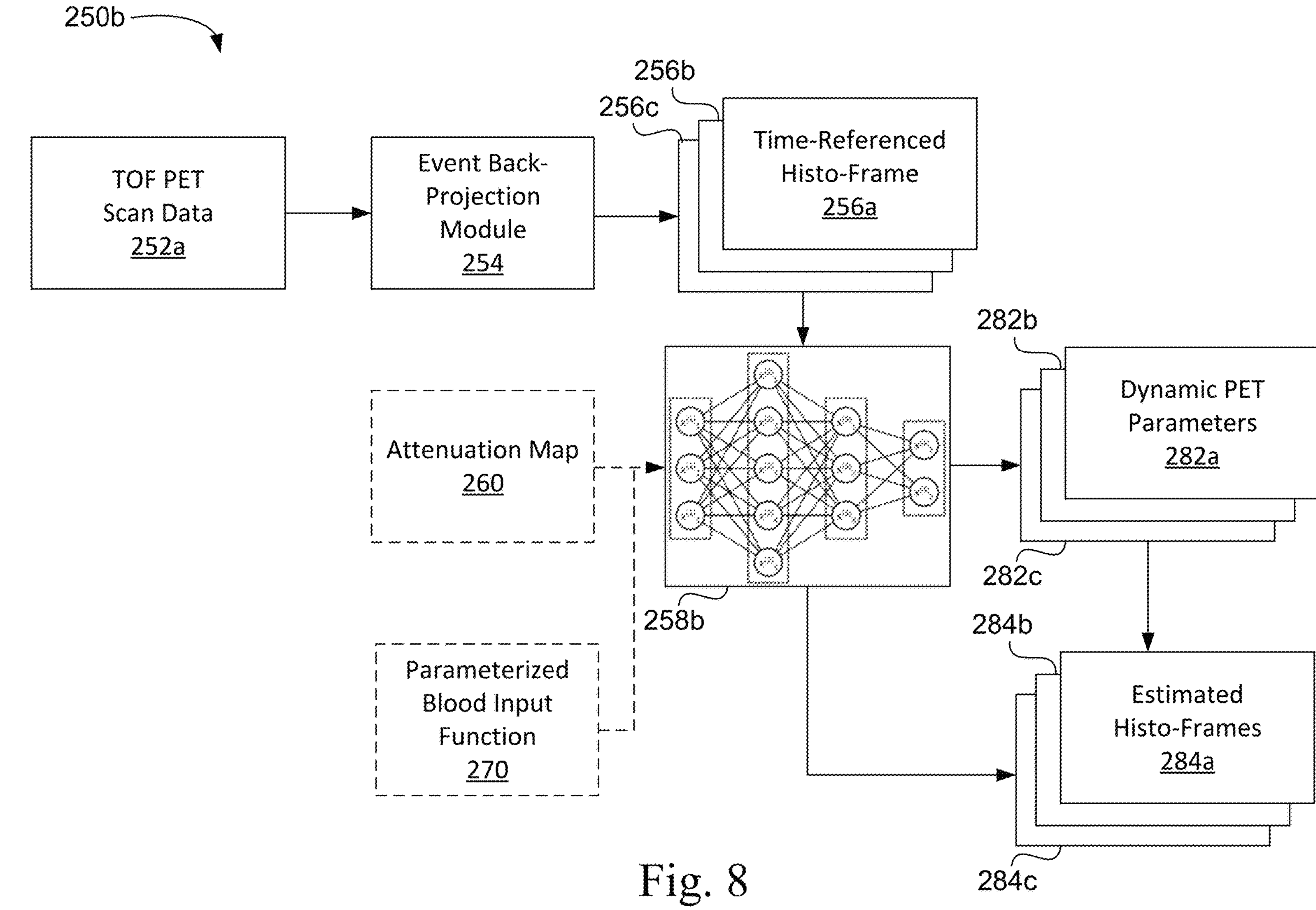
FIG. 8 is a block diagram illustrating a system configured to implement various portions of the method illustrated in FIG. 7, in accordance with some embodiments.

FIG. 7 is flowchart 200*b* illustrating a method of generating dynamic parameters of a PET scan using a trained neural network, in accordance with some embodiments. FIG. 8 is a block diagram illustrating a system 250*b* configured to implement various portions of the method illustrated in FIG. 7, in accordance with some embodiments. The method of generating dynamic parameters of PET data is discussed with reference to FIGS. 7 and 8. The method of generating dynamic parameters of a PET data is similar to the method of estimating parametric images discussed above with respect to FIG. 5. Similarly, the system 250*b* is similar to the system 250*a* discussed above with respect to FIG. 6. Similar description for the method and system is not repeated herein.

The method generating dynamic parameters of a PET data proceeds through steps 202-210, 216 discussed above with respect to FIG. 3. Accurate imaging time information is important for accurate results for estimated parametric imaging, since kinetic parameters, for example, metabolism rate, respiratory and/or cardiovascular phase, etc., are closely correlated to time information. The tracked time information in the time-referenced PET image data 252*a* provides a mechanism for tracking dynamic changes during data acquisition and to synchronize additional parameters, such as a blood input function, with the dynamic PET data.

In some embodiments, a trained neural network 258*b* is configured to utilize time-accurate information, such as position-time pairs as discussed above, to generate sets of dynamic PET parameters 282*a*-282*c*. As discussed in greater detail below, the trained neural network 258*b* is generated through an iterative training process using a training data set including time-referenced histo-image frames and/or time-referenced TOF PET data and correlated dynamic parameters (e.g., known kinetic parameters such as a change in histo-image frames over time). The trained neural network 258*b* is configured to receive time-referenced histo-image frames 256*a*-256*c* corresponding to at least one fixed axial position of the subject volume.

In some embodiments, the trained neural network 258*b* is configured to estimate histo-image frames 284*a*-284*c* at any given time point within the PET dataset 252*a* based on the dynamic PET parameters 282*a*-282*c* and a subset of the histo-image frames 256*a*-256*c* in the PET dataset 252. The trained neural network 258*b* is configured to use the dynamic PET parameters 282*a*-282*c* to estimate histo-image frames 284*a*-284*c* at times other than those included in the subset of the histo-image frames 254*a*-254*c*. In some embodiments, the dynamic PET parameters 282*a*-282*c* and/or estimated histo-image frames 284*a*-284*c* are utilized to create de-blurred images at additional time points without additional computational burdens (e.g., without using additional computational resources for those specific time periods).

In various embodiments, the trained neural network 258*b* may implement an indirect and/or direct parametric imaging process to generate the dynamic parameters. In an indirect parametric imaging process, parameters of a model are fitted into an image voxel value time sequence. In a direct parametric imaging process, model parameters are fitted directly to measured data (e.g., the TOF PET data and/or sinograms) instead of reconstructed images. The use of a kinetic image ensures time correlation among histo-image frames. In some embodiments, the training dataset for parametric image deblurring is available through full parametric image reconstruction. The trained neural network 258*b* provides decreased computation time to provide real-time dynamic imaging. The trained neural network 258*b* is configured to apply deblurring to a dynamically evolving image for dynamic imaging applications.

Figure 9:
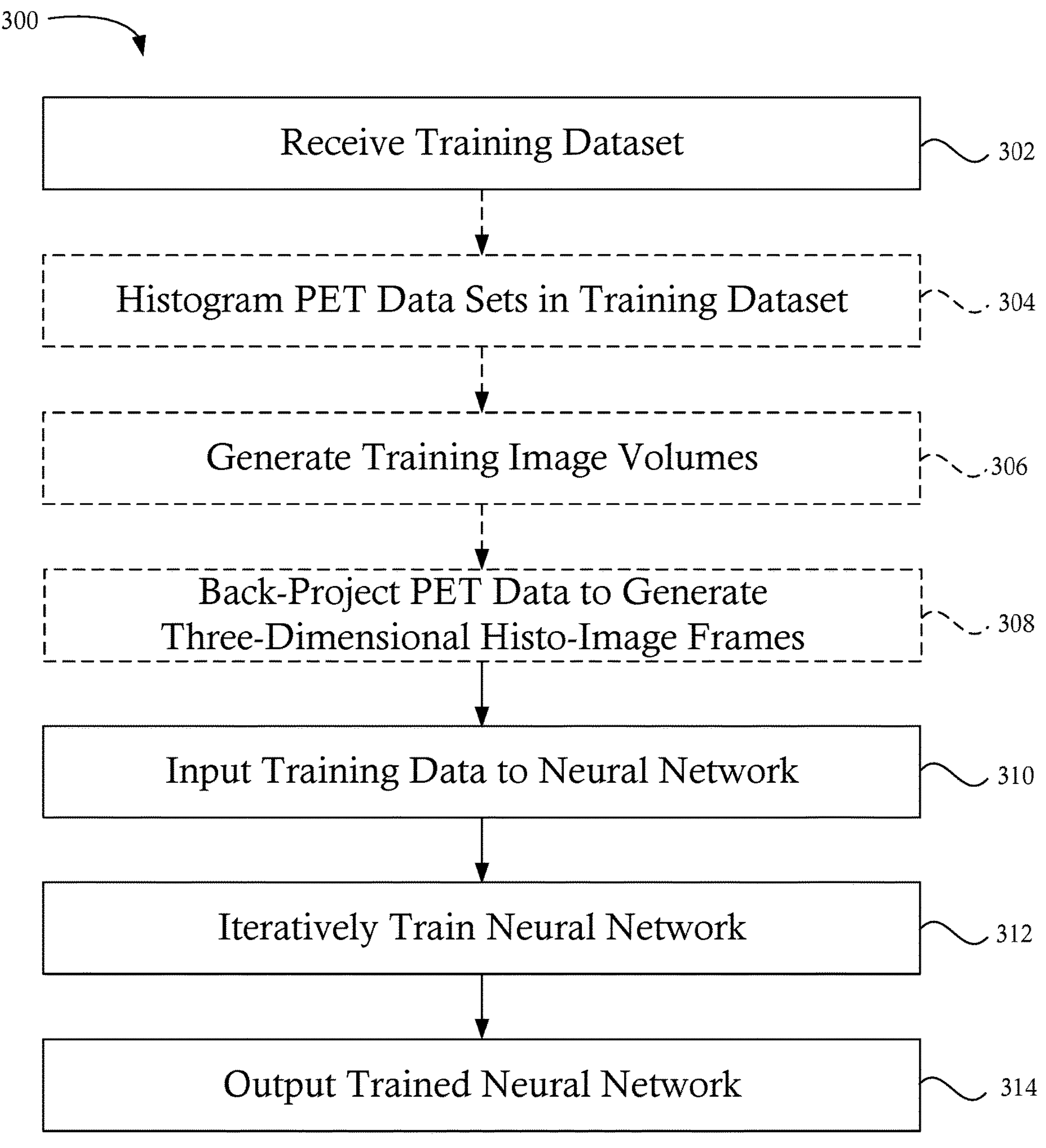
FIG. 9 is a flowchart illustrating a method of training a neural network, in accordance with various embodiments.
Figure 10:
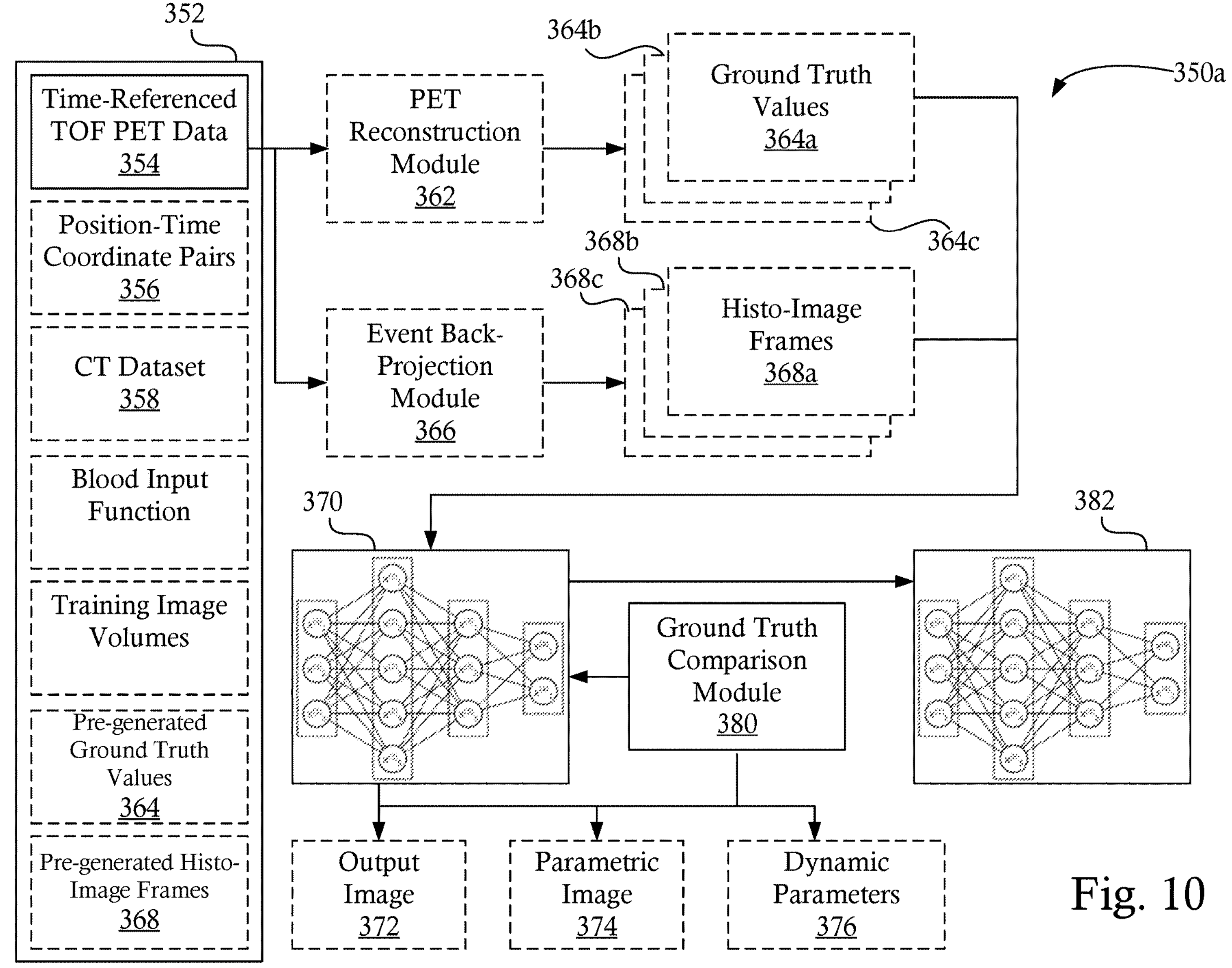
FIG. 10 is a process flow illustrating various steps of the method of training a neural network illustrated in FIG. 9, in accordance with some embodiments.

FIG. 9 is a flowchart 300 illustrating a method of training a neural network, in accordance with various embodiments. FIG. 10 is a process flow 350*a* illustrating various steps of the method of training a neural network illustrated in FIG. 9, in accordance with some embodiments. The method illustrated in FIG. 9 may be used to train any of the neural networks discussed herein, such as, for example, neural networks 258-258*b*, although it will be appreciated that the method of training a neural network may be configured to train any suitable neural network.

At step 302, a training data set 352 including a plurality of time-referenced TOF PET datasets 354 are acquired. The acquired time-referenced TOF PET datasets 354 may consist of PET acquisitions of list-mode data and/or may include PET sinograms generated from TOF PET list-mode data. In some embodiments, a set of position-time coordinate pairs 356 corresponding to the TOF PET datasets 354 (or integrated therein) are also received. An optional corresponding CT dataset 358 may also be acquired at step 302 for each PET dataset to provide for attenuation correction, as is known in the art.

The training dataset 352 may include data that is acquired from a repository of PET datasets, such as a training data database or other non-transitory storage mechanism. The training dataset 352 and/or each of the plurality of time-referenced TOF PET datasets 354, may depict any type of volumes and may have been acquired using any number of PET scanners and PET acquisition settings. In some embodiments, the acquired PET datasets are associated with a same volume (e.g., anatomical region), PET scanner and PET acquisition parameters as will be imaged/utilized using a trained neural network.

At optional step 304, each of the time-referenced TOF PET datasets 354 is histogrammed into TOF sinograms. At optional step 306, ground truth values **364*a*-364*c* are generated by a PET reconstruction module 362. In some embodiments, the PET reconstruction module 362 is configured to reconstruct the raw PET data (list-mode or sinogram) using one or more reconstruction algorithms that are or becomes known. Examples of such algorithms may include filtered back-projection (FBP) and ordered-subsets expectation maximization (OSEM). As is known in the art, the raw PET data may be subjected to various data processing algorithms (attenuation correction, motion correction, denoising, etc.) prior to reconstruction. In some embodiments, the PET reconstruction module 362 is configured to generate parametric PET reconstructions using one or more parametric reconstruction algorithms that are known or becomes known. Examples of such algorithms are disclosed in U.S. Pat. No. 10,722,789, which is incorporated herein by reference in its entirety. In some embodiments, the PET reconstruction module 362 is configured to generated dynamic PET parameters for each set of PET data in the training dataset 352**, for example, by performing a parametric PET reconstruction and extracting dynamic parameters from the reconstruction.

In some embodiments, steps 304 and/or 306 may be omitted and the training dataset 352 may include pre-generated TOF sinograms and/or pre-generated ground truth values 364. For example, in some embodiments, the pre-generated ground truth values 364 include ground truth images of the phantoms (or other volumes) use to generate the corresponding TOF PET data. As another example, the pre-generated ground truth values 364 include parametric images and/or dynamic PET parameters generated from parametric reconstructions using one or more known methods. It will be appreciated that any suitable pre-generated ground truth values 364 may be used based on the desired output of a trained neural network.

At optional step 308, each set of TOF sinograms and/or PET list-mode data is back-projected by an event back-projection module 366 into image space to generate a three-dimensional histo-image frames **368*a*-368*c* corresponding to specific axial positions (e.g., specific frames) in the TOF PET data. The TOF back-projection may be performed at step 308 using any suitable method, such as, for example, Joseph's method. In some embodiments, optional step 308 is omitted and the training dataset 352 includes pre-generated histo-image frames 368. If the training dataset 352 include pre-generated histo-image frames 368, the training dataset 352** may also omit raw PET data, such as list-mode PET data and/or TOF sinograms.

At step 310, each histo-image frame **368*a*-368*c* or pre-generated histo-image frames 368 (and, optionally, each corresponding mu-map) is input into an untrained and/or partially trained neural network 370 configured to generate a selected estimated output, such as, for example, one or more of an estimated output image volumes, one or more estimated parametric images, and/or estimated dynamic PET parameters. That is, the neural network 370 may generate an estimated output image volume 372 based on each input histo-image frame volume 368*a*-368*c* or pre-generated histo-image frames 368, an estimated parametric image 374 based on each input histo-image frame volume 368*a*-368*c* or pre-generated histo-image frames 368, and/or a set of estimated dynamic PET parameters 376 based on each input histo-image frame volume 368*a*-368*c* or pre-generated histo-image frames 368**.

At step 312, the neural network 370 is trained (e.g., iteratively modified) based on differences between the selected output (e.g., output image 372, parametric image 374, and/or dynamic parameters 376) and a ground truth **364*a*-364*c* or pre-generated ground truth 364. For example, in some embodiments, a ground truth comparison module 380 is configured to compare the ground truth values 364*a*-364*c* or pre-generated ground truth 364 with the output values to determine differences and provide modification values to the neural network 370. For example, in some embodiments, the ground truth comparison module 380 is configured to compare an estimated dynamic PET output for each TOF PET dataset (e.g., each dynamic PET dataset) to a corresponding dynamic PET output (e.g., dynamic PET parameters) from the plurality of dynamic PET outputs to determine any differences between each estimated dynamic PET output and the dynamic PET output that corresponds to the dynamic PET dataset that was inputted to the neural network. Although embodiments are illustrated with a separate ground truth comparison module 380, it will be appreciated that many neural network models are configured to perform ground truth comparison internally during a training process. The method iteratively repeats steps 310 and 312 until the neural network 370 produces an output within an acceptable range (e.g., being within a certain percentage error with respect to the ground truth values 364*a*-364*c* or pre-generated ground truth 364**).

The iterative training process illustrated in FIGS. 9-10 may utilize any suitable neural network training that is or becomes known. For example, a system configured to implement the iterative training process illustrated in FIGS. 9-10 may determine a loss based on a comparison between output image volumes 372 generated by the neural network 370 and corresponding ones of ground truth PET image volumes **364*a*-364*c*. The loss may comprise an L1 loss, and L2 loss, or any other suitable measure of total loss. An L1 loss is the sum of the absolute differences between each output image and its corresponding ground truth PET image, and an L2 loss is the sum of the squared differences between each output image and its corresponding ground truth PET image. In some embodiments, a training process similar to that described above in conjunction with FIG. 2** may be employed.

At step 312, the determined loss is back-propagated to the neural network 370, which changes its internal weights, or kernel parameter values, based on the back-propagated loss. Steps 310 and 312 may repeat until it is determined that the loss has reached an acceptable level or training otherwise terminates. At termination, the neural network 370 may be considered trained and, at step 314, a trained neural network 382 is output for use in one or more methods, such as those described in conjunction with FIGS. 3-6.

Figure 11:
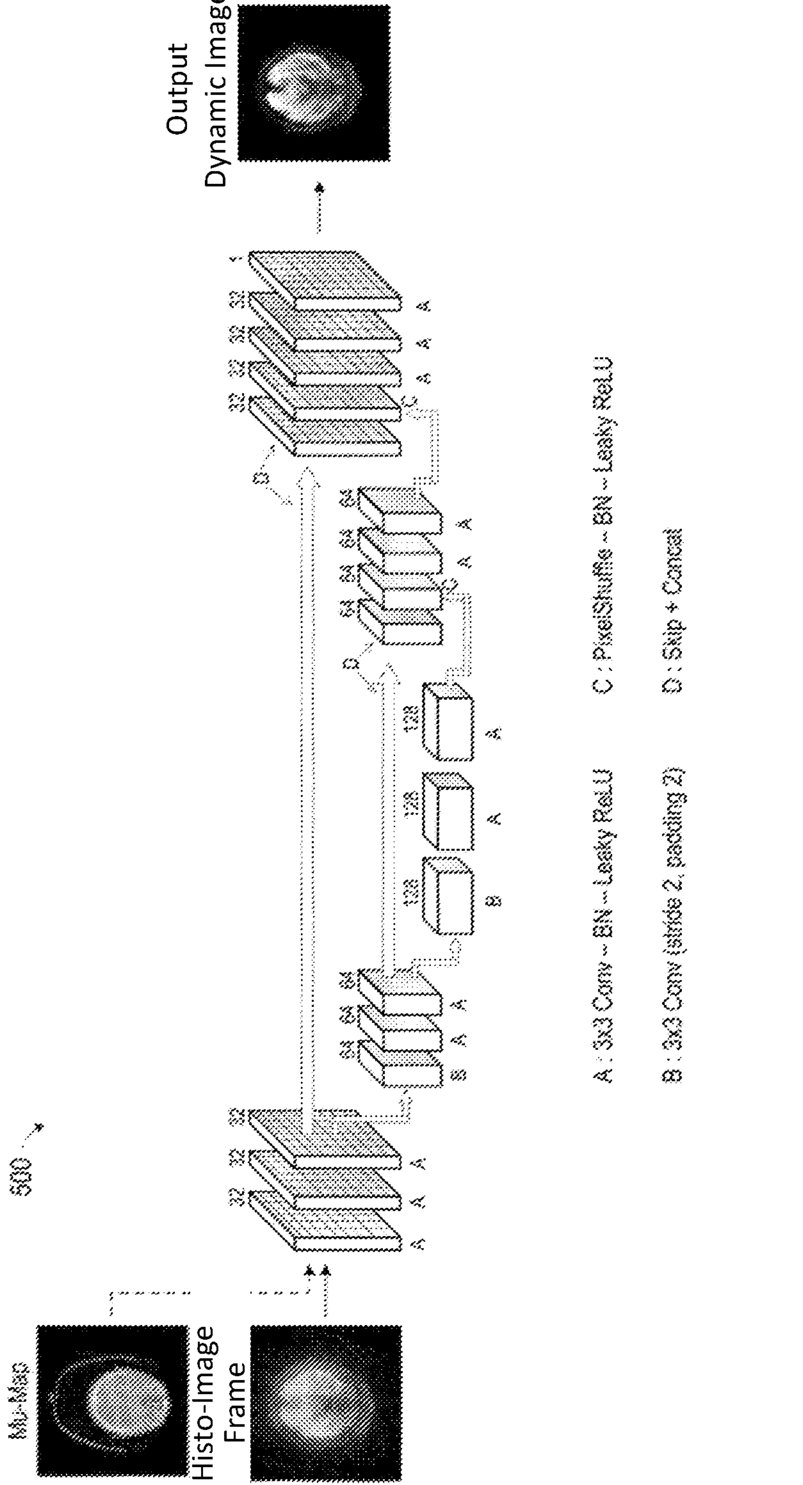
FIG. 11 illustrates a convolutional neural network architecture, according to some parameters.

The neural networks described herein may be implemented using any neural network architecture that is or becomes known. For example, as discussed above, FIG. 2 illustrates a neural network architecture 100 that may be implemented in some embodiments. Similarly, FIG. 11 illustrates neural network architecture 500 according to some embodiments. Architecture 500 is similar to a U-NET architecture but is fully convolutional. Specifically, the pooling of the U-Net architecture has been replaced with strided convolution and "up-convolution" has been replaced with the PixelShuffle up-sampling method. Embodiments are not limited to the specific elements of architecture 500.

According to some embodiments, training is performed at steps 310 and 312 using the Adam optimizer to minimize a balanced combination of mean absolute error (MAE) and multi-scale structural similarity difference (SSIM Δ) between a target PET image $x^{i*}$ and an output image $x_i=F_r(y_i)$ from histo-image frame $y_i$, with each frame containing p pixels. A corresponding loss function is shown below.

$$MAE = \frac{1}{p}\sum_{i=0}^{p1}|x_i - x_i^*|$$

$$SSIM\Delta = 1 - \frac{(2\mu_x^* + \mu_x + c_1)(2\sigma_x^* + \sigma_x + c_2)}{(\mu_x^{*2} + \mu_x^2 + c_1)(\sigma_x^{*2} + \sigma_x^2 + c_1)}$$

$$\alpha = \frac{\sum_{j=1}^{i+n-1} MAE_j}{\sum_{j=1}^{i+n-1} MAE_j + \sum_{j=1}^{i+n-1} SSIM\Delta_j}$$

$$\text{Loss} = (1-\alpha)MAE + \alpha SSIM\Delta$$

The above loss function dynamically balances the minimization of the absolute error between each corresponding pixel (i.e., MAE) and the perceptual loss function (SSIM), which evaluates the mean μ, variance σ 2 and covariance σ between the images. A running average of n samples of each loss type is used to calculate a balancing loss scalar α at each training step.

Figure 12:
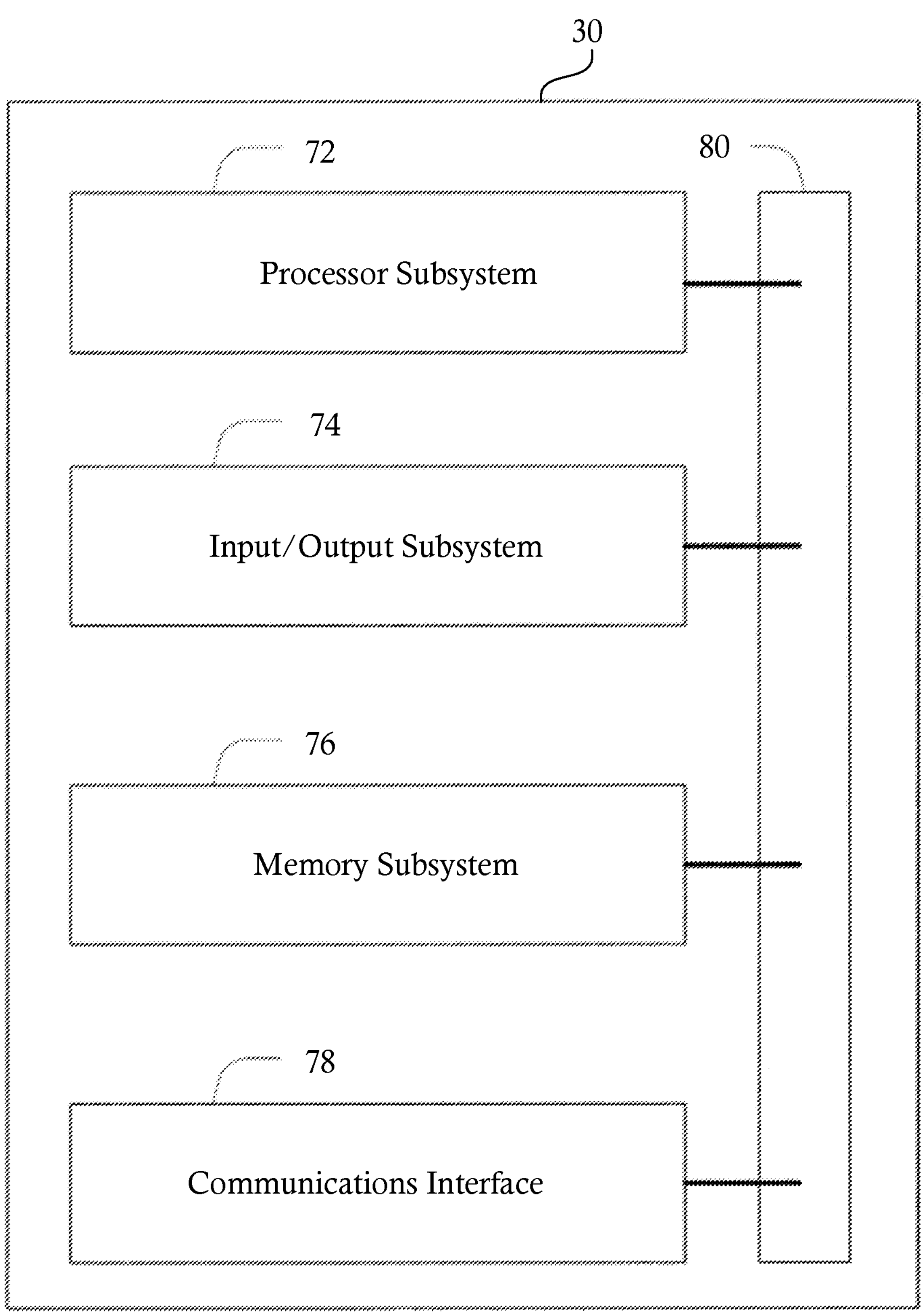
FIG. 12 illustrates a computer system configured to implement one or more processes, in accordance with some embodiments.

FIG. 12 illustrates a computer system 30 configured to implement one or more processes, in accordance with some embodiments. The system 30 is a representative device and can include a processor subsystem 72, an input/output subsystem 74, a memory subsystem 76, a communications interface 78, and a system bus 80. In some embodiments, one or more than one of the system 30 components can be combined or omitted such as, for example, not including an input/output subsystem 74. In some embodiments, the system 30 can comprise other components not shown in FIG. 12. For example, the system 30 can also include, for example, a power subsystem. In other embodiments, the system 30 can include several instances of a component shown in FIG. 12. For example, the system 30 can include multiple memory subsystems 76. For the sake of conciseness and clarity, and not limitation, one of each component is shown in FIG. 12.

The processor subsystem 72 can include any processing circuitry operative to control the operations and performance of the system 30. In various aspects, the processor subsystem 72 can be implemented as a general purpose processor, a chip multiprocessor (CMP), a dedicated processor, an embedded processor, a digital signal processor (DSP), a network processor, an input/output (I/O) processor, a media access control (MAC) processor, a radio baseband processor, a co-processor, a microprocessor such as a complex instruction set computer (CISC) microprocessor, a reduced instruction set computing (RISC) microprocessor, and/or a very long instruction word (VLIW) microprocessor, or other processing device. The processor subsystem 72 also can be implemented by a controller, a microcontroller, an application specific integrated circuit (ASIC), a field programmable gate array (FPGA), a programmable logic device (PLD), and so forth.

In various aspects, the processor subsystem 72 can be arranged to run an operating system (OS) and various applications. Examples of an OS comprise, for example, operating systems generally known under the trade name of Apple OS, Microsoft Windows OS, Android OS, Linux OS, and any other proprietary or open source OS. Examples of applications comprise, for example, network applications, local applications, data input/output applications, user interaction applications, etc.

In some embodiments, the system 30 can include a system bus 80 that couples various system components including the processing subsystem 72, the input/output subsystem 74, and the memory subsystem 76. The system bus 80 can be any of several types of bus structure(s) including a memory bus or memory controller, a peripheral bus or external bus, and/or a local bus using any variety of available bus architectures including, but not limited to, 9-bit bus, Industrial Standard Architecture (ISA), Micro-Channel Architecture (MSA), Extended ISA (EISA), Intelligent Drive Electronics (IDE), VESA Local Bus (VLB), Peripheral Component Interconnect Card International Association Bus (PCMCIA), Small Computers Interface (SCSI) or other proprietary bus, or any custom bus suitable for computing device applications.

In some embodiments, the input/output subsystem 74 can include any suitable mechanism or component to enable a user to provide input to system 30 and the system 30 to provide output to the user. For example, the input/output subsystem 74 can include any suitable input mechanism, including but not limited to, a button, keypad, keyboard, click wheel, touch screen, motion sensor, microphone, camera, etc.

In some embodiments, the input/output subsystem 74 can include a visual peripheral output device for providing a display visible to the user. For example, the visual peripheral output device can include a screen such as, for example, a Liquid Crystal Display (LCD) screen. As another example, the visual peripheral output device can include a movable display or projecting system for providing a display of content on a surface remote from the system 30. In some embodiments, the visual peripheral output device can include a coder/decoder, also known as Codecs, to convert digital media data into analog signals. For example, the visual peripheral output device can include video Codecs, audio Codecs, or any other suitable type of Codec.

The visual peripheral output device can include display drivers, circuitry for driving display drivers, or both. The visual peripheral output device can be operative to display content under the direction of the processor subsystem 72. For example, the visual peripheral output device can be able to play media playback information, application screens for application implemented on the system 30, information regarding ongoing communications operations, information regarding incoming communications requests, or device operation screens, to name only a few.

In some embodiments, the communications interface 78 can include any suitable hardware, software, or combination of hardware and software that is capable of coupling the system 30 to one or more networks and/or additional devices. The communications interface 78 can be arranged to operate with any suitable technique for controlling information signals using a desired set of communications protocols, services or operating procedures. The communications interface 78 can include the appropriate physical connectors to connect with a corresponding communications medium, whether wired or wireless.

Vehicles of communication comprise a network. In various aspects, the network can include local area networks (LAN) as well as wide area networks (WAN) including without limitation Internet, wired channels, wireless channels, communication devices including telephones, computers, wire, radio, optical or other electromagnetic channels, and combinations thereof, including other devices and/or components capable of/associated with communicating data. For example, the communication environments comprise in-body communications, various devices, and various modes of communications such as wireless communications, wired communications, and combinations of the same.

Wireless communication modes comprise any mode of communication between points (e.g., nodes) that utilize, at least in part, wireless technology including various protocols and combinations of protocols associated with wireless transmission, data, and devices. The points comprise, for example, wireless devices such as wireless headsets, audio and multimedia devices and equipment, such as audio players and multimedia players, telephones, including mobile telephones and cordless telephones, and computers and computer-related devices and components, such as printers, network-connected machinery, and/or any other suitable device or third-party device.

Wired communication modes comprise any mode of communication between points that utilize wired technology including various protocols and combinations of protocols associated with wired transmission, data, and devices. The points comprise, for example, devices such as audio and multimedia devices and equipment, such as audio players and multimedia players, telephones, including mobile telephones and cordless telephones, and computers and computer-related devices and components, such as printers, network-connected machinery, and/or any other suitable device or third-party device. In various implementations, the wired communication modules can communicate in accordance with a number of wired protocols. Examples of wired protocols can include Universal Serial Bus (USB) communication, RS-232, RS-422, RS-423, RS-485 serial protocols, FireWire, Ethernet, Fibre Channel, MIDI, ATA, Serial ATA, PCI Express, T-1 (and variants), Industry Standard Architecture (ISA) parallel communication, Small Computer System Interface (SCSI) communication, or Peripheral Component Interconnect (PCI) communication, to name only a few examples.

Accordingly, in various aspects, the communications interface 78 can include one or more interfaces such as, for example, a wireless communications interface, a wired communications interface, a network interface, a transmit interface, a receive interface, a media interface, a system interface, a component interface, a switching interface, a chip interface, a controller, and so forth. When implemented by a wireless device or within wireless system, for example, the communications interface 78 can include a wireless interface comprising one or more antennas, transmitters, receivers, transceivers, amplifiers, filters, control logic, and so forth.

In various aspects, the communications interface 78 can provide data communications functionality in accordance with a number of protocols. Examples of protocols can include various wireless local area network (WLAN) protocols, including the Institute of Electrical and Electronics Engineers (IEEE) 802.xx series of protocols, such as IEEE 802.11a/b/g/n/ac, IEEE 802.16, IEEE 802.20, and so forth. Other examples of wireless protocols can include various wireless wide area network (WWAN) protocols, such as GSM cellular radiotelephone system protocols with GPRS, CDMA cellular radiotelephone communication systems with 1×RTT, EDGE systems, EV-DO systems, EV-DV systems, HSDPA systems, and so forth. Further examples of wireless protocols can include wireless personal area network (PAN) protocols, such as an Infrared protocol, a protocol from the Bluetooth Special Interest Group (SIG) series of protocols (e.g., Bluetooth Specification versions 5.0, 6, 7, legacy Bluetooth protocols, etc.) as well as one or more Bluetooth Profiles, and so forth. Yet another example of wireless protocols can include near-field communication techniques and protocols, such as electro-magnetic induction (EMI) techniques. An example of EMI techniques can include passive or active radio-frequency identification (RFID) protocols and devices. Other suitable protocols can include Ultra Wide Band (UWB), Digital Office (DO), Digital Home, Trusted Platform Module (TPM), ZigBee, and so forth.

In some embodiments, at least one non-transitory computer-readable storage medium is provided having computer-executable instructions embodied thereon, wherein, when executed by at least one processor, the computer-executable instructions cause the at least one processor to perform embodiments of the methods described herein. This computer-readable storage medium can be embodied in memory subsystem 76.

In some embodiments, the memory subsystem 76 can include any machine-readable or computer-readable media capable of storing data, including both volatile/non-volatile memory and removable/non-removable memory. The memory subsystem 76 can include at least one non-volatile memory unit. The non-volatile memory unit is capable of storing one or more software programs. The software programs can contain, for example, applications, user data, device data, and/or configuration data, or combinations therefore, to name only a few. The software programs can contain instructions executable by the various components of the system 30.

In various aspects, the memory subsystem 76 can include any machine-readable or computer-readable media capable of storing data, including both volatile/non-volatile memory and removable/non-removable memory. For example, memory can include read-only memory (ROM), random-access memory (RAM), dynamic RAM (DRAM), Double-Data-Rate DRAM (DDR-RAM), synchronous DRAM (SDRAM), static RAM (SRAM), programmable ROM (PROM), erasable programmable ROM (EPROM), electrically erasable programmable ROM (EEPROM), flash memory (e.g., NOR or NAND flash memory), content addressable memory (CAM), polymer memory (e.g., ferroelectric polymer memory), phase-change memory (e.g., ovonic memory), ferroelectric memory, silicon-oxide-nitride-oxide-silicon (SONOS) memory, disk memory (e.g., floppy disk, hard drive, optical disk, magnetic disk), or card (e.g., magnetic card, optical card), or any other type of media suitable for storing information.

In one embodiment, the memory subsystem 76 can contain an instruction set, in the form of a file for executing various methods, such as methods including dynamic PET imaging using a trained neural network, as described herein. The instruction set can be stored in any acceptable form of machine readable instructions, including source code or various appropriate programming languages. Some examples of programming languages that can be used to store the instruction set comprise, but are not limited to: Java, C, C++, C #, Python, Objective-C, Visual Basic, or .NET programming. In some embodiments a compiler or interpreter is comprised to convert the instruction set into machine executable code for execution by the processing subsystem 72.

Each functional component described herein may be implemented in computer hardware, in program code, and/or in one or more computing systems executing such program code as is known in the art. As discussed above with respect to FIGS. 1 and 12, such a computing system may include one or more processing units which execute processor-executable program code stored in a memory system. Similarly, each of the disclosed methods and other processes described herein may be executed using any suitable combination of hardware and software. Software program code embodying these processes may be stored by any non-transitory tangible medium, as discussed above with respect to FIGS. 1 and 12.

Although the subject matter has been described in terms of exemplary embodiments, it is not limited thereto. Rather, the appended claims should be construed broadly, to include other variants and embodiments, which may be made by those skilled in the art.

What is claimed is:

1. A system, comprising:

a positron emission tomography (PET) imaging modality configured to execute a scan to acquire a PET dataset during an imaging period, wherein the PET dataset includes dynamic PET data having corresponding time-references and position-time coordinate pairs that track a position of a subject volume and time information during the scan; and a processor configured to:

back-project the PET dataset to generate a plurality of time-referenced histo-image frames, wherein each of the time-referenced histo-image frames corresponds to one of a plurality of specific axial positions imaged during a first sub-period of the imaging period determined by comparing corresponding time-references in the dynamic PET data with time information of the position-time coordinate pairs;

input each of the plurality of the time-referenced histo-image frames to a trained neural network;

generate, by the trained neural network, dynamic PET parameters for the PET dataset based on the time-referenced histo-image frames;

generate, by the trained neural network, at least one estimated PET histo-image frame using a subset of the plurality of time-referenced histo-image frames and the dynamic PET parameters, wherein the at least one estimated PET histo-image frame corresponds to a second sub-period of the imaging period not corresponding to the position-time coordinate pairs; and generate a plurality of time-specific reconstructed PET images using the trained neural network by converting at least one of the time-referenced histo-image frames or the at least one estimated PET histo-image frame into time-specific reconstructed PET images, wherein a period of each time-specific reconstructed PET image is the sub-period of a corresponding time-reference histo-image frame or estimated PET histo-image frame.

2. The system of claim 1, wherein the trained neural network is a trained convolutional neural network.

3. The system of claim 1, wherein the PET dataset comprises a list-mode dataset, a plurality of time-of-flight sinograms, or a combination thereof.

4. The system of claim 1, wherein the trained neural network is generated by a training dataset comprising a training input selected from the group consisting of: PET list-mode data, time-referenced time-of-flight sinograms, and time-referenced histo-image frames.

5. The system of claim 4, wherein the training dataset comprises a ground truth output image.

6. The system of claim 1, wherein each of the plurality of time-specific reconstructed PET images comprises:

an estimated output image based on each of the time-referenced histo-image frames having corresponding positions in the position-time coordinate pairs;

an estimated parametric image based on each of the time-referenced histo-image frames having corresponding positions in the position-time coordinate pairs; and a set of estimated dynamic PET parameters based on each of the time-referenced histo-image frames having corresponding positions in the position-time coordinate pairs.

7. The system of claim 6, wherein the trained neural network is trained based on differences between one or more of the estimated output image, the estimated parametric image, the estimated dynamic PET parameters, and a ground truth value.

8. A method of dynamic imaging for a positron emission tomography (PET) imaging device, comprising:

executing a scan to acquire a PET dataset during an imaging period, wherein the PET dataset includes dynamic PET data having corresponding time-references and position-time coordinate pairs that track a position of a subject volume and time information during the scan;

back-projecting the PET dataset to generate a plurality of time-referenced histo-image frames, wherein each of the time-referenced histo-image frames corresponds to one of a plurality of specific axial positions imaged during a first sub-period of the imaging period determined by comparing corresponding time-references in the dynamic PET data with time information of the position-time coordinate pairs;

inputting each of the plurality of time-referenced histo-image frames to a trained neural network;

generating, by the trained neural network, dynamic PET parameters for the PET dataset based on the time-referenced histo-image frames;

generating, by the trained neural network, at least one estimated PET histo-image frame using a subset of the plurality of time-referenced histo-image frames and the dynamic PET parameters, wherein the at least one estimated PET histo-image frame corresponding to a second sub-period of the imaging period not corresponding to the position-time coordinate pairs; and generating a plurality of time-specific reconstructed PET images using the trained neural network by converting at least one of the time-reference histo-image frames or the at least one estimated PET histo-image frame into time-specific reconstructed PET images, wherein a period of each time-specific reconstructed PET image is the sub-period of a corresponding time-reference histo-image frame or estimated PET histo-image frame.

9. The method of claim 8, wherein the at least one estimated PET histo-image frame comprises a set of estimated PET parameters based on each of the plurality of time-referenced histo-image frames.

10. The method of claim 8, wherein the trained neural network is a trained convolutional neural network.

11. The method of claim 8, wherein the PET dataset comprises a list-mode dataset.

12. The method of claim 8, wherein the PET dataset comprises a plurality of time-of-flight sinograms.

13. The method of claim 8, wherein the trained neural network is generated by a training dataset comprising a training input selected from the group consisting of: PET list-mode data, time-referenced time-of-flight sinograms, and time-referenced histo-image frames.

14. The method of claim 13, wherein the training dataset comprises a ground truth output image.

15. The method of claim 8, wherein each of the plurality of time-specific reconstructed PET images comprises:

an estimated output image based on each of the time-referenced histo-image frames having corresponding positions in the position-time coordinate pairs;

an estimated parametric image based on each of the time-referenced histo-image frames having corresponding positions in the position-time coordinate pairs; and a set of estimated dynamic PET parameters based on each of the time-referenced histo-image frames having corresponding positions in the position-time coordinate pairs.

16. The method of claim 15, wherein the trained neural network is trained based on differences between one or more of the estimated output image, the estimated parametric image, the estimated dynamic PET parameters, and a ground truth value.

17. A method of training a neural network for use in dynamic positron emission tomography (PET) imaging, comprising:

receiving a training dataset comprising a plurality of time-referenced histo-image frames and a plurality of ground-truth PET images, wherein each of the time-referenced histo-image frames is generated from dynamic PET data having corresponding time-references and position-time coordinate pairs identifying a position of a subject volume and time information for a PET imaging modality during acquisition of the dynamic PET data represented in a corresponding one of the plurality of time-referenced histo-image frames, and each of the time-referenced histo-image frames corresponding to one of the plurality of ground-truth PET images;

inputting each of the plurality of time-referenced histo-image frames to the neural network;

generating, by the neural network, dynamic PET parameters based on the plurality of time-referenced histo-image frames;

generating, by the neural network, at least one estimated PET histo-image frame using a subset of the plurality of time-referenced histo-image frames and the dynamic PET parameters, wherein the at least one estimated PET histo-image frame does not correspond to the position-time coordinate pairs;

generating, by the neural network, a plurality of time and position specific PET images for each of the plurality of time-referenced histo-image frames and the at least one estimated PET histo-image, and wherein each of the plurality of time and position specific PET images corresponds to at least one of the plurality of ground-truth PET images;

comparing the time and position specific PET images to the corresponding at least one of the ground-truth PET images; and modifying the neural network based on the comparison between the time and position specific PET images and the ground-truth PET images.

18. The method of claim 17, wherein each time and position specific PET images in the plurality of time and position specific PET images comprises one or more parameters.

* * * * *